United States Patent [19]
Loeb et al.

[11] Patent Number: 6,130,036
[45] Date of Patent: Oct. 10, 2000

[54] METHODS AND COMPOSITIONS FOR SCREENING FOR ANTI-AIDS DRUGS

[75] Inventors: Lawrence A. Loeb, Bellevue; Baek Kim, Mountlake Terrace, both of Wash.

[73] Assignee: University of Washington, Seattle, Wash.

[21] Appl. No.: 09/060,039

[22] Filed: Apr. 13, 1998

Related U.S. Application Data

[63] Continuation of application No. 08/741,605, Nov. 1, 1996, abandoned, which is a continuation of application No. 08/390,926, Feb. 17, 1995, abandoned, which is a continuation-in-part of application No. 08/198,814, Feb. 18, 1994, abandoned.

[51] Int. Cl.$^7$ ........................................................ C12Q 1/70
[52] U.S. Cl. .............................. 435/5; 435/6; 435/252.1; 435/91.2; 435/471; 424/9.2; 424/320.1
[58] Field of Search ................................. 435/5, 6, 252.1, 435/252.33, 91.2, 471; 424/9.2, 320.1

[56] References Cited

U.S. PATENT DOCUMENTS 5,026,687  6/1991  Yarchoan et al. ..................... 514/45

FOREIGN PATENT DOCUMENTS 1988-338051  10/1988  WIPO .
WO 95/22622  8/1995  WIPO .

OTHER PUBLICATIONS

Sweasy, J.B., Loeb, Lawrence, Mammalian DNA Polymerase B can Substitute for DNA Polymerase I during DNA Replication in *Escherichia coli,* Journal of Biological Chemistry, Jan. 25, 1992, 267(3), pp. 1407–1410.

Witkin, E.M., Roegner–Maniscalco, V., Overproduction of DnaE Protein (alpha Subunit of DNA Polymerase III) Restores Viability in a Conditionally Inviable *Escherichia coli* Strain Deficient in DNA Polymerase I, Journal of Bacteriology, Jun. 1992 174(12), pp.

Kellam, P., et al, Fifth mutation in human immunodeficiency virus type 1 reverse transcriptase contributes to the development of high–level resistance to zidovudine, Procs of the National Academy of Sciences of the USA, Mar. 1, 1992, 89(5) pp.1934–8.

Tsai, Che–chung, et al, In vitro screening for antiretroviral agents against simian immunodeficiency virus (SIV), Antiviral Research, 14 (Aug. 1990), pp.87–98.

Ahlering, T.E., et al, A new in vivo model to study invasion and metastasis of human bladder carcinoma, Cancer Research, Dec. 15, 1987, pp. 6660–6.

Vogt, M.W., et al., Treatment of HIV infections, Infectious Disease Clinics of NA, Jun. 1, 1987, pp. 323–39.

Kim and Loeb, "Human Immunodeficiency Virus Reverse transcriptase Substitutes For DNA Polymerase I in *Escherichia Coli,*" Proc. Natl. Acad. Sci. USA 92: 684–688, 1995.

Inouye et al., "Screening For Reverse Transcriptase Inhibitors And Anti–HIV Substances," *Journal Of Pharmaceutical Sciences* 76(11): p. S190, Abstract No. J 07–X–01, 1987.

*Primary Examiner*—John S. Brusca
*Assistant Examiner*—Stephen Siu
*Attorney, Agent, or Firm*—Seed Intellectual Property Law Group PLLC

[57] ABSTRACT

Methods and compositions related to AIDS are disclosed. Using the methods of the present invention, candidate compounds may be screened for the ability to inhibit reverse transcriptase of human immunodeficiency virus ("HIV RT"). Active HIV RT mutants may be detected by the disclosed methods. The present invention also discloses methods for screening for compounds that inhibit HIV RT obtained from an individual patient. In another aspect, methods for testing the biological effectiveness of candidate compounds for the inhibition of HIV RT in vivo are disclosed.

50 Claims, 7 Drawing Sheets

METHODS AND COMPOSITIONS FOR SCREENING FOR ANTI-AIDS DRUGS

CROSS-REFERENCE TO RELATED APPLICATIONS

This application is a continuation of U.S. patent application Ser. No. 08/741,605, filed Nov. 1, 1996, and abandoned; which application is a continuation of U.S. patent application Ser. No. 08/390,926, filed Feb. 17, 1995, and abandoned; which application is a continuation-in-part of U.S. patent application Ser. No. 08/198,814, filed Feb. 18, 1994 and abandoned.

FEDERAL FUNDING STATEMENT

This invention was made with government support under grant number R35CA39903 awarded by the National Cancer Institute of the National Institutes of Health. The government has certain rights in the invention.

TECHNICAL FIELD

The present invention is generally directed toward assays and compositions for identifying compounds for AIDS therapy. This invention is more particularly related to screening candidate compounds for the ability to inhibit reverse transcriptase of human immunodeficiency virus.

BACKGROUND OF THE INVENTION

Acquired Immune Deficiency Syndrome ("AIDS"), a fatal human disease, is generally considered to be one of the more significant diseases to affect humankind, and has affected numerous individuals worldwide. The disease appears to have originated in Africa and then spread to other locations, such as Europe, Haiti and the United States. AIDS began to be recognized as a distinct new disease in about the mid-1970s. The number of reported cases in the U.S. alone exceeds 100,000. The number of persons in just the U.S. who are infected has been estimated to be greater than one million.

Due to the devastating effect of AIDS on patients and indications that the disease is spreading, much effort has been devoted to elucidate and identify the cause of the disease. Epidemiological data suggested that AIDS is caused by an infectious agent that is transmitted by exposure to blood or blood products. Groups reported to be at greatest risk of contacting AIDS include homosexual or bisexual males and intravenous drug users. Hemophiliacs who receive blood products pooled from donors and recipients of multiple blood transfusions are also at risk.

AIDS is a disease that damages the body's immune system, leaving victims susceptible to opportunistic infections, malignancies or other pathological conditions against which a normal immune system would have protected the subject. After patients develop symptoms of AIDS, death generally occurs within 2–3 years of diagnosis. Clinical manifestations of the disease in its final stage include a collapse of a patient's immune defenses (which generally involves a depletion of helper T cells) accompanied by the appearance of a Kaposi sarcoma and/or various opportunistic infections. The pronounced depression of cellular immunity that occurs in patients with AIDS and the quantitative modifications of subpopulations of their T lymphocytes suggests that T cells or a subset of T cells are a central target for the infectious agent.

The etiology of AIDS and related disorders has been identified as being associated with infection by a new class of lymphotrophic retrovirus termed human immunodeficiency virus (HIV; known previously as HTLV or LAV). It appears that the virus is spread when body fluids, such as semen, vaginal fluids or blood, from an infected individual are passed to an uninfected person. As noted above, AIDS is characterized by a disorder associated with an impaired cell-mediated immunity and lymphopenia, in particular, depletion of those T cells that express the T4 (CD4) glycoprotein. This is due to the fact that HIV preferentially infects the CD4 lymphocyte population (CD4 cells). Both the binding of virus to susceptible target cells and the cell fusion that is a characteristic manifestation of HIV-induced cytopathology involve specific interactions between glycoproteins in the viral envelope and the cell surface of CD4 cells.

HIV contains two heavily glycosylated external envelope proteins, gp120 and gp41, which mediate attachment of virions to glycosylated cell surface receptor molecules. These glycoproteins are encoded by the env gene and translated as a precursor, gp160, which is subsequently cleaved into gp120 and gp41. Gp120 binds to the CD4 protein present on the surface of helper T lymphocytes, macrophages, and other cells, thus determining the tissue selectivity of viral infection.

The CD4 protein is a glycoprotein of approximately 60,000 molecular weight and is expressed on the cell membrane of mature, thymus-derived (T) lymphocytes, and to a lesser extent on cells of the monocyte/macrophage lineage. CD4 cells appear normally to function by providing an activating signal to B cells, by inducing T lymphocytes bearing the reciprocal CD8 marker to become cytotoxic/supressor cells, and/or by interacting with targets bearing major histocompatibility complex (MHC) class II molecules. The CD4 glycoprotein in addition to playing an important role in mediating cellular immunity also serves as the receptor for HIV. A variety of proposed therapeutic approaches have been based upon an attempt to disrupt the interaction of HIV gp120 with T cell CD4.

Once HIV has infected a cell, it replicates to increase the number of copies of the virus. Replication of the HIV genome proceeds by a series of enzymatic reactions involving two virus-encoded enzymes, reverse transcriptase ("HIV RT") and integrase, as well as host cell-encoded DNA polymerases and RNA polymerase. HIV RT polymerizes deoxyribonucleotides by using viral RNA as a template and also acts as a DNA polymerase by using the newly synthesized minus strand DNA as a template to produce a double-stranded DNA. Because of the essential role of HIV RT in the invasion of a host organism by the virus, therapeutic approaches have been based upon an attempt to inhibit HIV RT. The most useful drugs for the treatment of AIDS, such as azidothymidine ("AZT"), are nucleoside analogs directed against HIV RT. However, even these inhibitors of HIV RT have had limited success because of the extensive genetic variation and high mutation rate of HIV. Therefore, by rapid evolution of HIV, mutations in HIV RT arise frequently in infected individuals and render the virus resistant to nucleoside analogs and other antiviral therapies.

Although a few drugs such as AZT have prolonged the lives of some people with AIDS, there is presently no cure for AIDS. Therapeutic agents are needed for all stages of AIDS infections, to block action of the virus once infection has occurred, and to restore full function in patients whose immune systems have been damaged. Due to the limited success for previously suggested compositions for the treatment of AIDS, there is a need in the art for a method to screen for inhibitors of HIV RT and mutants thereof. The present invention fills this need, and further provides other related advantages.

SUMMARY OF THE INVENTION

Current methods in the art for the screening of compounds for their effectiveness in the treatment of AIDS rest heavily on the response of human or animal cells that contain the human immunodeficiency virus. This approach is hazardous in that laboratory personnel have the potential for exposure to a lethal infective agent and may account for the reluctance of investigators to test drugs against the AIDS virus. An advantage of the methods of the present invention is that the virus is not used.

Briefly stated, the present invention provides a variety of methods and compositions related to screening compounds for the ability to inhibit reverse transcriptase of human immunodeficiency virus and to screening for active reverse transcriptase mutants. In one aspect, the present invention provides methods of screening for compounds that inhibit reverse transcriptase of human immunodeficiency virus (HIV RT), comprising the steps of: (a) introducing a vector that expresses the gene encoding an HIV RT into a bacterial cell or eucaryotic cell in culture, the host cell containing a conditional mutant in the host cell gene encoding a DNA polymerase; (b) incubating the host cell harboring the vector under conditions that are limiting for the growth of a host cell in the absence of active HIV RT, the conditions further including a candidate compound which may be capable of inhibiting the HIV RT; and (c) detecting the presence or absence of growth, thereby determining whether the candidate compound inhibited the HIV RT.

In a preferred embodiment, the method comprises the steps of: (a) introducing a vector that expresses the gene encoding an HIV RT into temperature sensitive E coli polA12recA718 cells, the host cells containing a conditional mutant in the host cell gene encoding a DNA polymerase such that growth of the host cells at a non-permissive temperature is dependent on expression of active HIV RT; (b) plating dilutions of the host cells harboring the vector onto a plate containing media sufficient for growth and containing a candidate compound which may be capable of inhibiting the HIV RT; (c) incubating the host cells harboring the vector at a temperature not permissive for growth of E. coli polA12recA718 cells that lack a DNA-dependent DNA polymerase activity at the non-permissive temperature; and (d) detecting the presence or absence of growth at low cell density, thereby determining whether the candidate compound inhibited the HIV RT.

The present invention provides in another aspect E. coli polA12recA718 cells that harbor an HIV RT plasmid (pHIV RT).

In another aspect, the present invention provides methods of screening for active HIV RT mutants, comprising the steps of: (a) introducing a vector that expresses the gene encoding an HIV RT mutant into a bacterial cell or eucaryotic cell in culture, the host cell containing a conditional mutant in the host cell gene encoding a DNA polymerase; (b) incubating the host cell harboring the vector under conditions that are limiting for the growth of a host cell in the absence of active HIV RT; and (c) detecting the presence or absence of growth, thereby determining whether the HIV RT mutant is active.

In a preferred embodiment, the method comprises the steps of: (a) introducing a vector that expresses the gene encoding an HIV RT mutant into temperature sensitive E. coli polA12recA718 cells, the host cells containing a conditional mutant in the host cell gene encoding a DNA polymerase such that growth of the host cells at a non-permissive temperature is dependent on expression of active HIV RT; (b) plating dilutions of the host cells harboring the vector onto a plate containing media sufficient for growth; (c) incubating the host cells harboring the vector at a temperature not permissive for growth of E. coli polA12recA718 cells that lack a DNA-dependent DNA polymerase activity at the non-permissive temperature; and (d) detecting the presence or absence of growth at low cell density, thereby determining whether the HIV RT mutant is active.

In another aspect, the present invention provides methods of screening for compounds that inhibit HIV RT obtained from a patient, comprising the steps of: (a) amplifying the gene for HIV RT from a sample from an individual infected with HIV; (b) introducing the HIV RT gene into a vector that expresses the HIV RT gene; (c) introducing the vector into a bacterial cell or eucaryotic cell in culture, the host cell containing a conditional mutant in the host cell gene encoding a DNA polymerase; (d) incubating the host cell harboring the vector under conditions that are limiting for the growth of a host cell in the absence of active HIV RT, the conditions further including a candidate compound which may be capable of inhibiting the HIV RT; and (e) detecting the presence or absence of growth, thereby determining whether the candidate compound inhibited the HIV RT from the individual.

In a preferred embodiment, the method comprises the steps of: (a) amplifying the gene for HIV RT from a sample from an individual infected with HIV; (b) introducing the HIV RT gene into a vector that expresses the HIV RT gene; (c) introducing the vector into temperature sensitive E. coli polA12recA718 cells, the host cells containing a conditional mutant in the host cell gene encoding a DNA polymerase such that growth of the host cells at a non-permissive temperature is dependent on expression of active HIV RT; (d) plating dilutions of the host cells harboring the vector onto a plate containing media sufficient for growth and containing a candidate compound which may be capable of inhibiting the HIV RT; (e) incubating the host cells harboring the vector at a temperature not permissive for growth of E. coli polA12recA718 cells that lack a DNA-dependent DNA polymerase activity at the non-permissive temperature; and (f) detecting the presence or absence of growth at low cell density, thereby determining whether the candidate compound inhibited the HIV RT from the individual.

In yet another aspect, the present invention provides methods for assessing the biological effectiveness of candidate compounds. In one embodiment, a method for testing the biological effectiveness of candidate compounds for the inhibition of human immunodeficiency virus reverse transcriptase (HIV RT) in vivo, comprises: (a) introducing cells containing a vector that expresses the gene encoding an HIV RT into a test animal, the cells containing a conditional mutant in the cell gene encoding a DNA polymerase such that survival of the cells in the animal is dependent on expression of active HIV RT; (b) administering to the animal a compound in a pharmaceutically acceptable form, the compound a candidate for the inhibition of HIV RT; and (c) assessing the ability of the candidate compound to clear the cells from the animal, thereby determining whether the candidate compound inhibits HIV RT in vivo.

In another embodiment, a method for detecting in a blood sample from a warm-blooded animal the presence of an active compound that inhibits human immunodeficiency virus reverse transcriptase (HIV RT), comprises: (a) administering to a warm-blooded animal a compound that inhibits HIV RT, the compound in a pharmaceutically acceptable form; (b) isolating a blood sample from the animal; and (c)

detecting the presence or absence of the compound by testing the blood sample in the method according to claim 1 wherein the blood sample replaces the candidate compound of the method, thereby determining whether the compound is present in active form in the blood of the animal.

These and other aspects of the present invention will become evident upon reference to the following detailed description and attached drawings. All publications and patents are incorporated in their entirety herein by reference.

BRIEF DESCRIPTION OF THE DRAWINGS

FIG. 5A illustrates ddC effect on growth of Pol I$^{ts}$ cells containing pHIV RT-2 at 30° C. (closed circle) or 37° C. (open circle). FIG. 5B illustrates ddC effect on growth of Pol I$^{ts}$ cells containing pRT-TK at 30° C. (closed circle) or 37° C. (open circle). FIG. 5C illustrates AZT effect on growth of Pol I$^{ts}$ cells containing pHIV RT-2 at 30° C. (closed circle) or 37° C. (open circle). FIG. 5D illustrates AZT effect on growth of Pol I$^{ts}$ cells containing pRT-TK at 30° C. (closed circle) or 37° C. (open circle).

DETAILED DESCRIPTION OF THE INVENTION

Figure 1:
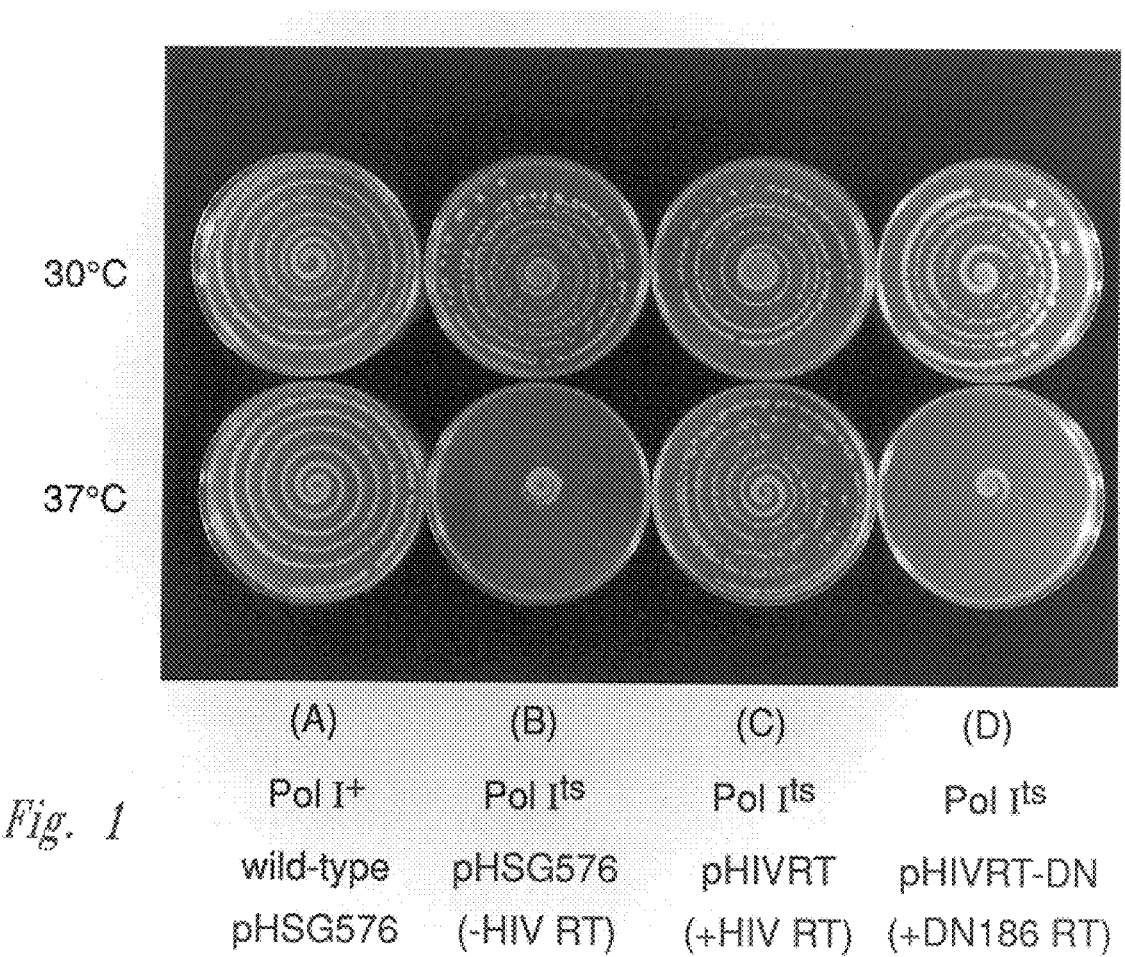
FIGS. 1A–1D demonstrate the functional complementation of *E. coli* DNA polymerase I by HIV reverse transcriptase. (A) Growth of the wild-type *E. coli* polA+recA+ with the parent plasmid, pHSG576, at 30° C. and 37° C. (B) Growth of polA12recA718 with pHSG576 at 30° C. and 37° C. (C) Growth of polA12recA718 with pHIV RT at 30° C. and 37° C. (D) Growth of polA12recA718 with pHIV RT-DN at 30° C. and 37° C. *E. coli* polA+recA+ (JS295) and polA12recA718 (JS200) were transformed with pHSG576, a low copy number plasmid containing a Pol I independent pSC101 replication origin and a chloramphenicol resistance gene (Takeshida et al., *Gene* 71:63–74, 1987). The polA12recA718 strain (tet$^R$) was transformed with pHIV RT-2 and pHIV RT-DN. pHIV RT-DN expresses D186N HIV RT mutant protein that is not functional (Larder et al., *Proc. Natl. Acad. Sci. USA* 86:4803–4807, 1989). Transformed cells were grown to log phase in nutrient broth containing tetracycline (7.5 mg/ml), chloramphenicol (34 mg/ml) and IPTG (1 mM) and then 2×10$^6$ cells were deposited and diluted by rotation with a 10 µl inoculation loop on a nutrient agar plate containing the same concentrations of tetracycline, chloramphenicol and IPTG. Duplicate plates were incubated at 30° C. and 37° C. for 48 hrs.

The disclosure of the present invention shows that reverse transcriptase of human immunodeficiency virus (hereinafter referred to as "HIV RT") is able to functionally complement host cells containing a conditional mutant in the host cell gene encoding a DNA polymerase, and that this functional complementation has a number of uses related to AIDS. In particular, the present invention is directed toward methods and compositions useful for screening compounds for the ability to inhibit HIV RT, for screening for active HIV RT mutants, for screening a patient's HIV RT to tailor the individual's therapeutic regime, and for assessing the biological effectiveness of anti-HIV RT compounds.

A wide variety of cells may be used as the host cell in the methods of the present invention, and include bacterial cells and eucaryotic cells. Examples of suitable host cells include bacteria such as *E. coli*, Salmonella (e.g., *typhimurium*), Bacillus (e.g., *subtilis*), Thermus (e.g., *aquaticus*), yeast such as Saccharomyces (e.g., *cerevisiae*), and mammalian cells such as hamster cells, human cells, and rat cells, which have been engineered to contain a conditional mutant in the gene encoding a DNA polymerase. Briefly, two methodologies are commonly used for the production of conditional mutants in DNA polymerases. In one method, cells are exposed to mutagenic agents, screened for the mutants defective in DNA synthesis at non-permissive conditions and then analyzed for mutations in DNA polymerases (e.g., Liu et al., *Proc. Natl. Acad. Sci. USA* 80:797–801, 1983). Alternatively, a DNA polymerase gene may be cloned, the gene altered to produce mutations (e.g., using site-specific mutagenesis) and then transferred to wild type cells for gene displacement or disruption by transposons (e.g., Sweasy et al., *Proc. Natl Acad. Sci. USA* 90:4626–4630, 1993). A preferred host cell containing a conditional mutant in the gene encoding a DNA polymerase is *E. coli* polA12recA718. This mutant contains a temperature sensitive (ts) DNA polymerase I (Pol I$^{ts}$) mutation (Witkin et al., *J Bacteriol.* 174:4166–4168, 1992). It is unable to grow at 42° C. in rich media at low density due to a failure to join Okazaki fragments during lagging strand DNA synthesis (Sweasy et al., *J. Biol. Chem.* 267:1407–1409, 1992).

As disclosed within the present invention, introduction of a HIV RT gene into a host cell containing such a conditional mutant ("host cell") is able to genetically complement the host cell such that HIV RT substitutes for the deficient DNA polymerase in promoting cell growth and in plasmid replication. The term "HIV RT gene" as used herein includes an intact gene as well as portions thereof which encode a polypeptide capable of exhibiting DNA-dependent DNA polymerase activity. For example, Skalka et al. (*Reverse Transcriptase*, Cold Spring Harbor Laboratory Press, pp. 144–150, 1993) describe deletions of portions of HIV RT without loss of polymerase activity. Ways to prepare an HIV RT gene include isolation or amplification from a biological sample, or recombinant methodology, or synthetic production. For example, an HIV RT gene may be prepared from a patient's blood sample (Saiki et al., *Science* 230:1350–1354, 1985), from recombinant HIV RT (Kim et al., *Proc. Natl. Acad. Sci. USA* 92:684–688, 1995), or by homologous recombination of virus (Kellam et al., *Proc. Nati. Acad. Sci. USA* 89:1934–1938, 1992). An HIV RT gene is generally introduced into a host cell via a vector. Examples of suitable vectors include plasmids, bacteriophages, viruses, cosmids, etc. An HIV RT gene may be introduced into a vector by a variety of means well known to those in the art (e.g., Sambrook et al., *Molecular Cloning. A Laboratory Manual*, Cold Spring Harbor Laboratory Press, 1989). For example, a vector may be cut with restriction enzyme(s) and the HIV RT gene ligated into the vector. After a vector is prepared that expresses a gene encoding an HIV RT, the vector is introduced into a host cell by a variety of means well known to those in the art (Sambrook et al., ibid.). In a preferred embodiment, an HIV RT gene is introduced into *E. coli* polA12recA718 cells using an HIV RT expressing plasmid, hereinafter referred to as "(pHIV RT)". Particularly preferred polA12recA718 strains are those harboring a (pHIV RT) plasmid designated as pHIV RT-1, pHIV RT-2, and pHIV RT-3, having American Type Culture Collection (ATCC) accession numbers of ATCC 69568, ATCC 69569, and ATCC 69570, respectively.

It may be desirable for a host cell to contain one or more additional genes encoding an enzyme (such as a kinase) able to phosphorylate nucleosides and/or nucleotides in order to increase the likelihood of finding, through the use of the methods of the present invention, a compound that inhibits HIV RT. For example, human or viral genes encoding enzymes with such capabilities (e.g., human thymidine kinase, cytidine kinase, deoxycytidine kinase, guanosine kinase, deoxyguanosine kinase, and nucleotide and deoxynucleotide kinases) may be introduced into a host cell by means such as those described above. Such a gene(s) encoding an enzyme(s) for phosphorylation is conveniently introduced into a host cell via a single vector that expresses both the gene(s) and an HIV RT gene. Alternatively, a kinase gene may be inserted into the genome of a host cell. It will be evident to those of ordinary skill in the art that a gene need not be intact but may be a portion thereof (e.g., truncated version of intact molecule), provided that the polypeptide expressed is capable of phosphorylation activity. For example, a portion of the intact thymidine kinase gene (e.g., as described in Munir et al., *Proc. Natl. Acad. Sci. USA* 90:4012–4016, 1993) may be used.

To assess whether a host cell possesses (via expression by a vector introduced) active HIV RT for screening of candidate inhibitory compounds, host cells harboring a vector that expresses the gene encoding an HIV RT are incubated under conditions that are limiting for the growth of a host cell in the absence of active HIV RT. A variety of limiting conditions may be utilized within the methods of the present invention. For example, the conditions may be limiting for growth in the absence of replication of the plasmid where such replication requires a DNA polymerase for replication. In this embodiment, host cells are susceptible to an inhibitor (such as an antibiotic) in the absence of replication of the plasmid, which bears a gene conferring upon the host cells resistance to the inhibitor. A gene, such as a chloramphenicol resistance gene, which confers resistance may be introduced into a vector (and then into host cells via the vector) by means such as those described above. Active HIV RT, which has been introduced into the host cells via a vector, provides the DNA polymerase activity required for replication of the plasmid bearing the gene which confers resistance to an inhibitor of host cell growth. Thus, host cells possessing active HIV RT will be able to grow in the presence of an inhibitor of host cell growth (by replication of a plasmid bearing a gene which confers resistance to the inhibitor).

Another example of a condition that is limiting for the growth of a host cell is a temperature which is not permissive for growth of cells that lack a DNA-dependent DNA polymerase activity. In this embodiment, growth of host cells at a non-permissive temperature is dependent on expression of active HIV RT. For example, host cells may grow at a lower temperature (such as 30° C.) even in the absence of a DNA-dependent DNA polymerase activity. However, at a higher temperature (e.g., 42° C.), the host cells either do not grow or may require high cell density to grow. Whether the lack of growth of particular host cells at a non-permissive temperature is host cell density independent (i.e., no growth regardless of cell density) or density dependent (e.g., no growth provided cell density is low) may be readily ascertained by examining the host cells under both low and high cell density conditions. Alternatively, if one does not wish to determine whether lack of growth of host cells at a non-permissive temperature is density dependent or density independent, one may simply always grow the host cells at low cell density since even those host cells whose growth at a non-permissive temperature is density dependent do not grow at a low cell density. It will be evident to those of ordinary skill in the art that other means are suitable for limiting the growth of a host cell in the methods of the present invention.

A compound which is a candidate for the inhibition of HIV RT (hereinafter referred to as "candidate compound") is tested in the methods of the present invention using a host cell described above. A candidate compound is included in the incubation conditions which are limiting for the growth of a host cell in the absence of active HIV RT. It may be desirable to test a variety of different (e.g., graded) amounts of a candidate compound. Alternatively, more than one candidate compound may be included. In addition, one or more candidate compounds may be tested in combination with one or more traditional anti-AIDS compounds, such as azidothymidine ("AZT"). Any compound is a candidate compound. Nucleosides and nucleotides, which herein include analogs of either, are examples of candidate compounds. A candidate compound may be isolated from a natural source or prepared synthetically, including by recombinant, enzymatic and/or synthetic chemical means. Candidate compounds may be designed (e.g., based on structure-function studies), generated randomly, or produced by a combination of these approaches. As used herein, inhibition of HIV RT by a candidate compound refers to reducing or eliminating the DNA synthesis catalyzed by HIV RT. A candidate compound may inhibit HIV RT in a variety of ways, including by binding to HIV RT or by terminating DNA synthesis catalyzed by HIV RT.

Whether a candidate compound inhibits the HIV RT expressed in host cells is readily ascertained by detecting the presence or absence of cell growth when the compound is present. An absence of cell growth indicates that the host cells were limited by the inhibition of HIV RT by the candidate compound. It may be desirable to confirm that the lack of host cell growth is due to the inhibition of HIV RT, rather than an indirect affect on the host cell. Such confirmation may be readily accomplished by the testing of one or more appropriate controls. For example, one may show that the candidate compound does not inhibit the growth of a host cell that does not contain a conditional mutant in the host cell gene for which HIV RT provides functional complementation of the defect. A convenient method for ascertaining growth is to plate concentric dilutions of host cells in solid selection plates. A variety of other means of plating or growing cells in liquid culture, such as tritiated thymidine incorporation, PCR of sequences and FACS sorting, may be used as well as other methods known to those of ordinary skill in the art. Growth of cells may be assessed visually.

In another aspect, the methods of the present invention may be used to screen for active HIV RT mutants. A gene encoding a HIV RT mutant may be an intact gene, or portion thereof, which contains one or more mutations. Ways to prepare such a gene include isolation or amplification from a biological sample, or recombinant methodology, or synthetic production (e.g., synthetic assembly or in vitro mutagenesis). Methodologies for the preparation of mutant genes are well known to those of ordinary skill in the art (e.g., Ausubel et al., *Short Protocols in Molecular Biology*, 2d ed., Greene Publishing Associates and John Wiley & Son, 1993; Munir et al., *Proc. Natl. Acad. Sci. USA* 90:4012–4016, 1993). Active HIV RT mutants are those mutants which possess DNA polymerase activity. By use of the methods of the present invention as described above, a HIV RT mutant that is active functionally complements the DNA polymerase defect of a host cell. The complementation permits growth of the host cell under conditions that are limiting for its growth in the absence of active HIV RT. An example of an active HIV RT mutant is that contained on a plasmid designated as pHIV RT-4. *E. coli* that express this HIV RT mutant are resistant to AZT. For example, a polA12recA718 strain harboring (PHIV RT-4), ATCC accession number ATCC 69571, is resistant to AZT.

The genetic selection assays disclosed herein permit the collection of a large number of mutant HIV RTs. Extensive mutagenesis of HIV RT enables the development of structure-function relationships that are essential to understanding evolution of HIV RT and to designing compounds which avoid evasion by mutations in HIV RT. The complementation system disclosed herein may be used to predict the likelihood that mutations would arise that render HIV RT resistant to specific compounds or combinations. A library of active HIV RT mutants may be used in the methods of the present invention to screen for a compound or combination of compounds that inhibit all or most of the mutants. Alternatively, a library of active HIV RT mutants may permit design of a compound or combination of compounds as inhibitors to the class of mutants. A combination of compounds with different spectrums of resistant mutations may be used together (combination chemotherapy) to mitigate against the emergence of resistant strains.

In another aspect, the present invention provides methods of screening for compounds that inhibit HIV RT obtained from an individual infected with HIV. This permits a therapeutic regime to be tailored to an individual patient. The methods disclosed herein may be used prior to commencing therapy with an anti-HIV RT compound to determine whether the compound is effective against the HIV RT residing in the particular patient. Similarly, it may be desirable to test the compound against the patient's HIV RT after commencing therapy so as to monitor for the development of an HIV RT mutant that is resistant to the compound. Mutations in HIV RT frequently emerge during the course of infection and render the virus resistant to current therapies. Thus, the methods of the present invention may be used to evaluate HIV RT in a patient with AIDS for the presence of mutations that render the virus resistant to specific compounds used in the treatment of the individual patient, and to evaluate the therapeutic effectiveness of candidate compounds.

Sources of a sample containing a gene encoding HIV RT from an individual infected with HIV include biological fluids (e.g., blood) and tissue. The gene for HIV RT may be amplified from a sample using a variety of methods well known to those in the art. For example, an HIV RT gene may be amplified by a polymerase chain reaction ("PCR" (see Mullis et al., U.S. Pat. Nos. 4,683,195; 4,683,202 and 4,800,159)). A patient's HIV RT gene is introduced into a host cell via a vector as described above. Such a gene may be an intact gene or portion thereof. Host cells harboring such a vector are incubated under limiting conditions, as described above, and in the presence of one or more candidate compounds, as also described above, which may be capable of inhibiting the patient's HIV RT. The ability of a compound (or combination of compounds) to inhibit a patient's HIV RT is determined based on whether the presence or absence of growth of the host cells is detected.

In another aspect, the present invention provides methods for testing the biological effectiveness of candidate compounds for the inhibition of HIV RT in vivo. Cells, containing a vector that expresses a gene encoding an HIV RT and a conditional mutant in the cell gene encoding a DNA polymerase, are prepared as described above. Such cells (e.g., bacterial cells or yeast cells) are introduced into a test animal. The cells may be introduced by a variety of means including injection and ingestion. Examples of test animals include mice, rats, guinea pigs, rabbits, cats, dogs, swine and non-human primates such as monkeys. The conditional mutant in the cell gene encoding a DNA polymerase renders the survival of the cells in the test animal dependent on expression of active HIV RT. One or more candidate compounds are administered to the test animal to determine whether the compound or combination of compounds inhibits HIV RT in vivo. A compound may be administered by a variety of routes including injection, orally or transdermally. A compound is generally formulated in a pharmaceutically acceptable form for administration, and it will be evident to those in the art that the form may depend on the physical-chemical properties of the compound and its route of adsorption into the bloodstream.

Following the administration of a compound or combination of compounds to a test animal, the ability of the compound(s) to clear the introduced cells from the test animal is assessed. Such assessment may be performed once after an appropriate time to permit clearance, or may be performed at two or more time intervals until the cells have been cleared or the maximum appropriate time for clearance has been reached. It will be evident to those of ordinary skill in the art that an assessment of cell clearance from a test animal may be performed in a variety of ways. For example, assays typically used for such purposes include removal from the test animal of a blood sample which is then tested for the presence of HIV RT-dependent cells by a variety of tests that include microbiological culture, colony formation on appropriate selective microbiological media, PCR analysis of DNA-specific gene sequences for the introduced cells, fluorescent-activated cell sorting (FACS) analysis using fluorescently-tagged monoclonal antibodies specific for the introduced cells, or reverse transcriptase activity.

Alternatively, where the cells introduced in a test animal are pathogenic to the animal, the ability of a compound(s) to clear the cells may be assessed based upon the presence or absence of the pathogenic condition. Further, a pathogenic condition may be fatal, so that survival of the test animal is dependent on clearance of the introduced cells. Therefore, under such circumstances, simply assessing the enhanced survival of the test animal is a direct assay of the effectiveness of a candidate compound in blocking test cell growth, i.e., in inhibiting the activity of HIV RT itself. In a preferred embodiment, the test animal is a mouse and the cells introduced are derived from *Salmonella typhimurium*. Because *S. typhimurium* is fatal to mice, the survival of the test animal is dependent upon the clearance of the bacterial cells. Confirmation that survival of the test animal is dependent on the administration of a compound or combination of compounds is readily demonstrated by the inability of test animals, who are inoculated with bacterial cells, to survive in the absence of administration of the compound(s).

In another embodiment, the introduced cells are used indirectly to assay the level of candidate compound(s) circulating in the blood of a test animal. This is done by removing blood samples from test animals at a single or multiple times following administration of the compound, or mixture of compounds, and then assessing the anti-HIV RT activity of the compounds present in the blood by their ability to inhibit cell growth in vitro, in an assay as described above. This test may be used to assess directly the bioavailability of candidate compounds and their pharmacokinetic parameters. Thus, subsequent metabolism of candidate compounds and their inactivation (or activation) is monitored speedily and safely without the need for exposing either test animals or laboratory and medical personnel to active virus. Application of this particular embodiment to human clinical trials of an anti-HIV RT compound makes possible the direct determination of the bioavailability of the compound and its subsequent pharmacokinetics, both in healthy volunteers as well as HIV-positive individuals.

The following examples are offered by way of illustration and not by way of limitation.

EXAMPLES

Example I

Screening Assay for Compounds that Inhibit HIV Reverse Transcriptase (HIV RT)

A. Strains and Plasmids 1. polA12recA718 (PolI$^{ts}$) *Escherichia coli* strain (*E. coli*): This is strain SC18-12 derived from *E. coli* B/r and has the following genotype:

recA718 polA12 uvrA155 trpE65 lon-11 sulA1 (Witkin and Roegner-Maniscalco, *J Bacteriol.* 174:4166–4168, 1992). This *E. coli* double mutant polA12recA718 contains a temperature sensitive (ts) DNA polymerase I (Pol I$^{ts}$) mutation. It is unable to grow at 42° C. in rich media at low cell density due to a failure of Pol I to join Okazaki fragments during lagging strand DNA synthesis. For polA12 single mutant, wild-type *E. coli* cells (MM300) are mutagenized by nitrosoguanidine (Monk and Kinross, *J Bact.* 109:971–978, 1972). Mutagenized cells are screened for sensitivity to MMS (methyl methane sulfonate) at 32 (or 30) and 42 (or 37)° C. in replica plates. The polA12 mutant shows MMS sensitivity only at 42° C. Next, polA12 single mutant is combined with recA718 mutant SC18 for polA12 recA718 double mutant (Witkin and Roegner-Maniscalco, 1992).

2. pHSG576 Plasmid: pHSG576 is a low copy number plasmid that is replicated in DNA polymerase I (Pol I) independent manner (Takeshida et al., *Gene* 71:63–74, 1987). This plasmid contains lacP/O, a lacZ gene fragment that can be scored as a target for mutagenesis by alpha complementation, and also contains a segment with a multiple cloning site. pHSG576 is constructed by combining pSC101 replication origin, the multiple cloning site with lacP/O from pUC8/9 for a-complementation and a chloramphenicol resistant gene. In particular, HaeII fragment of pSC101 replication origin of pHSG415r (Brady et al., *Gene* 27:223–232, 1984), HhaI (Alton and Vapnek, *Nature* 282:864–869, 1979)-HaeII Tn9-Cm$^R$ fragment in pHSG439 (Brady et al., 1984) and HaeII lacZ' fragment of pUC8 or pUC9 (Vieira and Messing, *Gene* 19:259, 1982) are combined for pHSG576 construction.

3. pHIV RT Plasmids: pHIV RT plasmids are pHSG576 derivatives expressing different level of HIV RT. The HIV RT gene, fused to a ribosomal binding site (RBS) for expression, was obtained from S. Wilson. This fused HIV RT gene was cloned into pHSG576 between the Hind III and Eco RI restriction sites, generating (pHIV RT-1). pHIV RT-2 is the same as pHIV RT-1, except that it contains a 61 bp insert between lacP/O and HIV RT gene. pHIV RT-3 is the same as pHIV RT-1, except that it contains a 431 bp insert encoding a 94 amino acid long amino terminal (N-T) of mouse DNA polymerase beta (pol beta) from pBL (Sweasy and Loeb, *Proc. Natl. Acad. Sci. USA* 90:4626–4630, 1993) at Hind III site of pHIV RT-1. pHIV RT-3 expresses HIV RT fused to N-terminal 94 amino acids of the DNA polymerase beta gene.

pHIV RT-1, -2 and -3 were prepared as follows:

a. pHIV RT-1: HIV RT gene was amplified from pRT with 5' RT primer and 3' RT primer. The 5' primer is: 5' GAA GAT CTA AGC TTA GGA GGT TGT CCC ATA TGC CCA TTA GTC C 3' (SEQ ID No. 1). The 3' primer is: 5' TTT TGA ATT CGC ATG CCT GCA G 3' (SEQ ID No. 2). The 5' RT primer contains the sequence that is complementary to 5' end of RT gene, ribosomal binding sequence for protein expression and Hind III. The 3' RT primer contains the sequence that is complementary to 3' end sequence of RT gene in pRT and Eco RI. Amplified DNA was subjected to Hind III and Eco RI enzymes and ligated to pHSG576.

b. pHIV RT-2: 61 bp non-coding sequence was inserted to Hind III site of pHIV RT-1. Insertion of this DNA fragment decreases the protein expression level about three fold, as estimated by western analysis.

c. pHIV RT-3: 431 bp Hind III fragment of pBL encoding N-terminal 94 amino acid sequence was inserted to Hind III site of pHIV RT- 1. Insertion of this fragment produces two different HIV RT proteins. One is a fusion protein (M.W. about 77 Kdal) and the other is wild-type HIV RT protein. Expression level of both protein about ⅙ of the protein expressed from pHIV RT- 1.

4. Transformation of Plasmid to Pol I$^{ts}$ cells. The parent plasmid (pHSC576) or pHIV RT was introduced into polA12recA718 cells by electroporation. Pol I$^{ts}$ cells are grown in nutrient broth media (NB, 8 g/l Difco nutrient broth and 4 g/l NaCl) until the optical density of the cell culture is at 600 nm (O.D. 600) is 0.5. Cells are harvested and washed by autoclaved water three times. Plasmid DNAs are transformed into the washed cell by electroporation as described (Ausubel et al., *Short Protocols in Molecular Biology*, 2d ed., Greene Publishing Associates and John Wiley & Son, 1-26-1-27, 1993). DNA should be prepared in *E. coli* B strain to get high transformation efficiency ($1 \times 10^9$ cells/ug). Transformed cells are plated onto NA selection plates that contain Difco nutrient agar (11.5 g/l), NaCl (5 g/l) tetracycline (12.5 mg/l), chloramphenicol (34 mg/l) and IPTG (1 mM). Plates are incubated at 30° C. for 24 hours.

B. Complementation of Pol I$^{ts}$ mutant by HIV RT

1. Cell Preparation. Pol I$^{ts}$ mutant cells containing pHSG576, pβL (Sweasy et al., *Proc. Natl. Acad. Sci. USA* 90:4626–4630, 1993) and pHIV RT plasmids are grown in NB selection media (NB media with 12.5 mg/l tetracycline, 34 mg/l chloramphenicol and 1 mM IPTG) to O.D. of 0.6.

2. Complementation Test.

a. Qualitative Test:

*E. coli* polA12 single mutant can form single colonies in rich media and low cell density at 42° C., whereas polA12recA718 double mutant cannot. In polA12 single mutant, single strand gaps produced by polA12 mutation can be filled by RecA with its recombination repair function, which allows this polA12 single mutant to grow at 42° C. (Witkin and Roegner-Maniscalco, *J. Bacteriol.* 174:4166–4168, 1992). However, in recA718 mutant, the level of RecA function was decreased. Therefore, in polA12recA718 double mutant, single strand gaps produced by polA12 mutation cannot be repaired, which results in failure of the double mutant to grow as single colonies at high temperatures.

The cell density-dependent temperature-sensitive phenotype is demonstrated in FIG. 1(A) by plating concentric dilutions of *E. coli* polA12recA718 in NA selection plates (Witkin and Roegner-Maniscalco, *J. Bacteriol.* 174:4166–4168, 1992). A variety of other methods of plating or growing the cells in liquid culture known to those in the art can be utilized. In this example, about $2 \times 10^6$ *E. coli* cells were introduced at the center of a plate using a 10 μl inoculation loop. The plate was rotated and the loop was gradually moved to the outside of the plate to display the bacteria in a diverging spiral of increasing dilution. Wild type *E. coli*, polA$^+$recA$^+$ (Pol I$^+$), containing the parent plasmid (pHSG576) that lacks the HIV RT gene (Takeshida et al., *Gene* 71:63–74, 1987) is able to grow both at 30° C. and 37° C. (FIG. 1A), whereas the Pol I$^{ts}$ mutant containing the parent plasmid (pHSG576) lacking the HIV RT gene grows at 30° C. at all dilutions tested, but can only grow at 37° C. at the high density in the center of the plate (FIG. 1B). This growth deficit can be complemented in the Pol I$^{ts}$ mutant by a plasmid expressing HIV RT (pHIVRT-2); the infected *E. coli* are able to grow at 37° C. at low density near the periphery of the plate (FIG. 1C). HIV RT DN186 contains a mutation at the substrate binding site and expresses a non-functional reverse transcriptase. As seen in FIG. 1D, the *E. coli* double mutant harboring the plasmid that expresses DN186 HIV RT (pHIVRT-DN) is unable to grow at 37° C., further indicating that genetic complementation of DNA polymerase I by HIV RT requires that HIV RT is active.

b. Quantitative Test:

To quantitate the efficiency with which HIV RT substitutes for DNA polymerase I, the plating efficiencies at 30° C. and 37° C. using the Pol I$^{ts}$ mutant harboring either pHSG576 or pHIV RT are determined (FIG. 2). polA12recA718 strain containing either pHSG576 or pHIV RT-2 (HIV RT$^+$) is grown to $2 \times 10^8$ cells per ml at 30° C. The indicated numbers of cells per plate in progressive dilutions (1 to 1/16) are plated on nutrient agar containing tetracycline, chloramphenicol and IPTG as described in FIG. 1. Duplicate plates are incubated for 48 hours at 30° C. (black bar) or 37° C. (open bar) and the number of colonies were scored. In this example, the ts phenotype of polA12recA718 mutant is observed at 37° C. and HIV RT complements ts the Pol I$^{ts}$ defect. As cell density decreases, *E. coli* with pHSG576 are progressively unable to grow at 37° C. (compare the number of colonies at 30° C. and 37° C. in FIG. 2). In contrast, *E. coli* expressing HIV RT form an equal number of colonies at 30° C. and 37° C. (FIG. 2). This experiment provides an example that expression of HIV RT is able to fully complements the growth defect exhibited by the polA12recA718 strain. For comparison, Pol I$^+$ mutant harboring pHSG576 also gives high plating efficiency close to 1 at all dilutions and 37° C.

pHIV RT-1 and pHIV RT-2 plasmids gave about 60% and 90% plating efficiency at 37° C. at low cell density plate (500 cell per plate). The same type of experiment was done with the polA12recA718 strain expressing rat DNA polymerase β (Sweasy et al., *J. Biol. Chem.* 267:1407–1409, 1992). The plating efficiency at dilution 5 (about 150 cells per plate) of the Pol I$^{ts}$ strain expressing rat DNA pol β at 42° C. was about 60% to 80% of that obtained at 30° C. In NA plates without IPTG, the plating efficiency of the Pol I$^{ts}$ cell expressing rat pol β drastically decreased at low cell density, as was observed for Pol I$^{ts}$ cells containing pHSG576.

A number of other assays can be utilized for the quantitation of the ability of HIV RT or different mutants of HIV RT to complement the temperature-sensitive phenotype of bacteria that have mutations in one or more of the genes that code for DNA polymerase. These include but are not limited to: turbidity of culture, plaque formation, and incorporation of radioactive precursors such as $^3$H-thymidine into DNA.

C. Inhibition by AZT of Complementation of *E. coli* DNA Polymerase I by HIV RT

The assay to measure inhibition of complementation consists of growing the HIV RT expressing cells at elevated temperature that is restrictive for a temperature-sensitive mutant of DNA polymerase I and then determining the extent of inhibition of cell growth by compounds that inhibit HIV RT.

Figure 2:
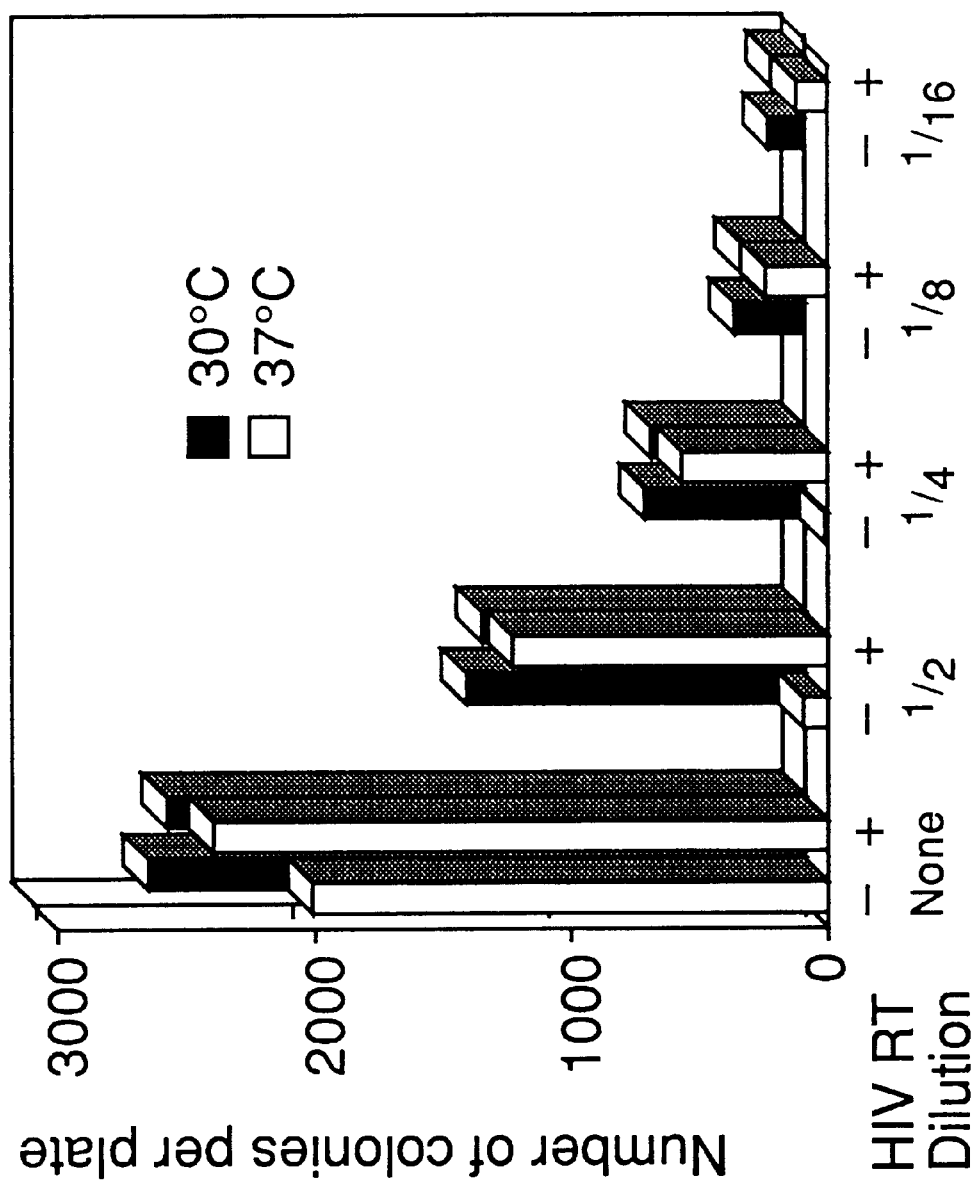
FIG. 2 graphically illustrates the efficiency of substitution of HIV RT for DNA Pol I. *E. coli* polA12recA718 containing either pHSG576 or pHIV-RT was grown to 2×10$^8$ cells per ml at 30° C. The indicated number of cells per plate in progressive dilutions was plated on nutrient agar containing tetracycline, chloramphenicol and IPTG as described in FIG. 1. Duplicate plates were incubated for 48 hrs. at 30° C. (black bar) or 37° C. (open bar) and colonies were scored. The results given are averages from three different experiments.
Figure 3A:
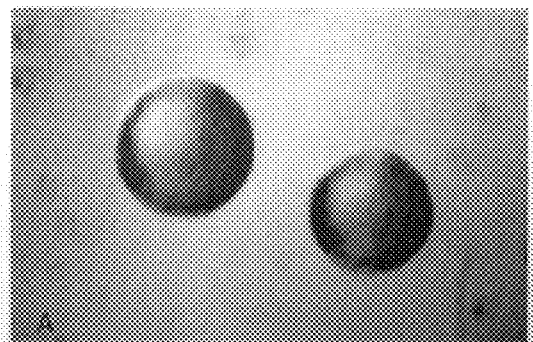
FIGS. 3A–3E show the inhibition of HIV RT complementation by AZT. (A)polA+recA+ with pHSG576, grown on nutrient agar with 100 nM AZT (AZT-NA) at 37° C. (B) polA12recA718 expressing HIV RT on nutrient agar without AZT at 37° C. (C)polA12recA718 expressing HIV RT on AZT-NA at 37° C. (D)polA12recA718 expressing HIV RT on AZT-NA at 30° C. (E)polA12recA718 expressing rat DNA polymerase β on AZT-NA at 37° C. Approximately 200 *E. coli* cells harboring the designated plasmids (pBL and pHIV RT-3) were plated in duplicate on NA plates containing tetracycline, chloramphenicol and IPTG (as described in FIG. 1) with or without AZT (85 nM) and were incubated at 30° C. or 37° C. for 38 hours. The relative magnification of the colonies is 25×.
Figure 3B:
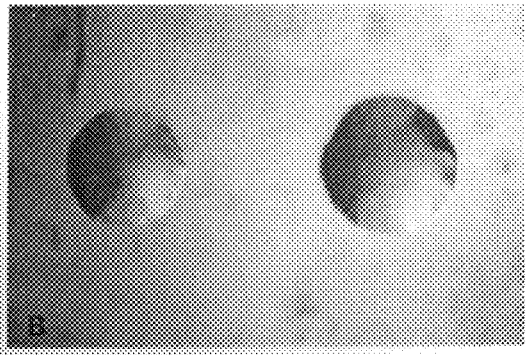
Figure 3C:
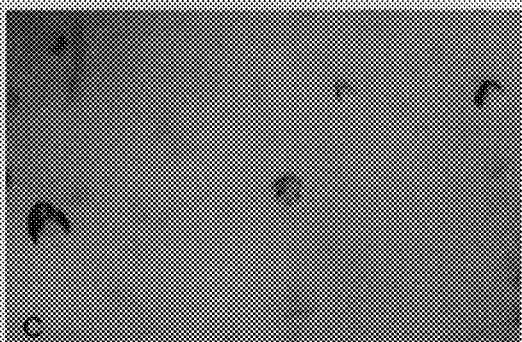
Figure 3D:
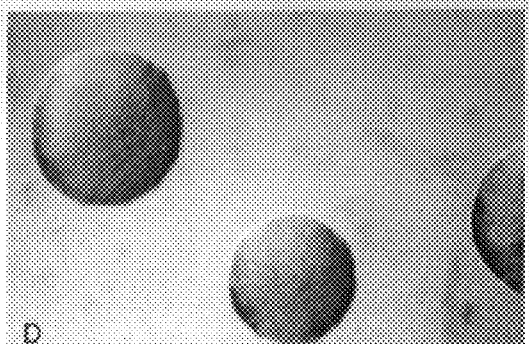
Figure 3E:
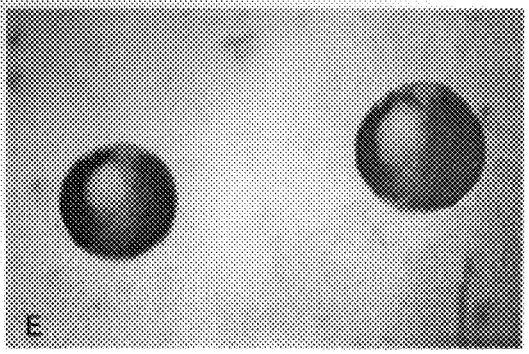

Approximately 200 *E. coli* cells are diluted from the fresh culture, harboring plasmids that either lack or contain the gene for HIV RT and plated in duplicate on NA plates containing tetracycline, chloramphenicol and IPTG (as described in FIG. 1). The plasmid harboring *E. coli* are grown with or without AZT (100 nM) at 30° C. or 37° C. for 36 hours. pHIV RT-1 and pHIV RT-2 gave about the same sensitivities as pHIV RT-3. The wild type strain forms large smooth colonies on nutrient agar containing 85 nM AZT at 37° C. (FIG. 3(A)) and also at 30° C. The Pol I$^{ts}$ strain harboring pHIV RT forms visually similar colonies at 37° C. in the absence of AZT (FIG. 3(B)). However, in the presence of AZT, Pol I$^{ts}$ cells expressing HIV RT form only miniature colonies at 37° C. (FIG. 3(C)). At 30° C., where Pol I is fully active, the Pol I$^{ts}$ strain containing pHIV RT forms large colonies even in the presence of AZT (FIG. 3(D)). As a control in this experiment, it is demonstrated that complementation of the Pol I defect by DNA polymerase β does not render it sensitive to AZT (FIG. 3(E)). These results are in accord with the known preferential incorporation of AZT by HIV RT compared to that exhibited by DNA polymerase β (Copeland et al., *J. Biol. Chem.* 267:21459–21464, 1992). The demonstration of the absence of susceptibility of pol-β to a candidate compound or combination of compounds serves a safety control as it indicates that a patient's natural DNA polymerases will not be inhibited by the compound(s). The AZT once incorporated acts as chain terminator and presumably prevents DNA replication. The range of AZT concentrations in nutrient agar that differentiates between strains expressing HIV RT and Pol β is 40–120 nM. The effectiveness of different nucleotide analogs is ascertained by incubating the cells on nutrient agar containing graded concentrations of the chemicals to be tested as potential drugs for the treatment of AIDS.

Figure 4A:
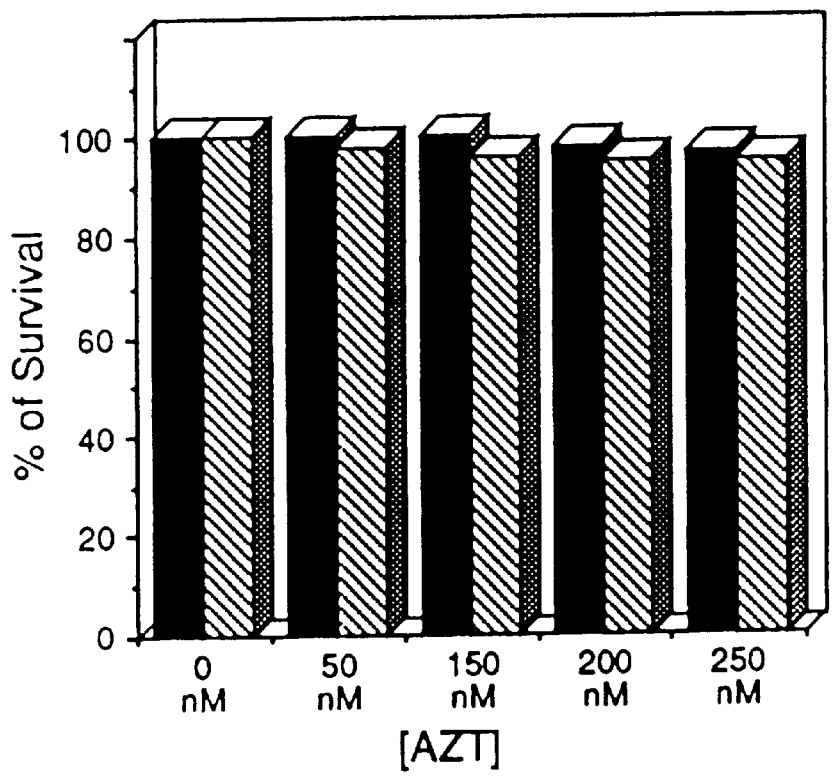
FIGS. 4A–4C illustrate inhibition of complementation of HIV reverse transcriptase by AZT. (A)polA12recA718 expressing rat DNA polymerase β. (B)polA12rec718 expressing HIV RT from pHIV RT-2. (C)polA12recA718 expressing T215Y HIV RT mutant protein that shows resistance to AZT (St. Clair et al., *Science* 253:1557–1559, 1991). Approximately 300 *E. coli* cells expressing the designated proteins were plated in duplicate on nutrient agar containing tetracycline, chloramphenicol and IPTG (as described in FIG. 1) and AZT (0, 50, 150, 200 and 250 nM) and were incubated at 30° C. (black bar) or 37° C. (open bar) for 48 hr. The percent survival is the ratio of colonies formed in the presence and absence of AZT. In studies similar to those in FIG. 1, T215Y HIV RT mutant from pHIVRT-TY is able to complement the growth defect of Pol I$^{ts}$ mutant at non-permissive temperature to the same extent as the wild-type HIV RT.
Figure 4B:
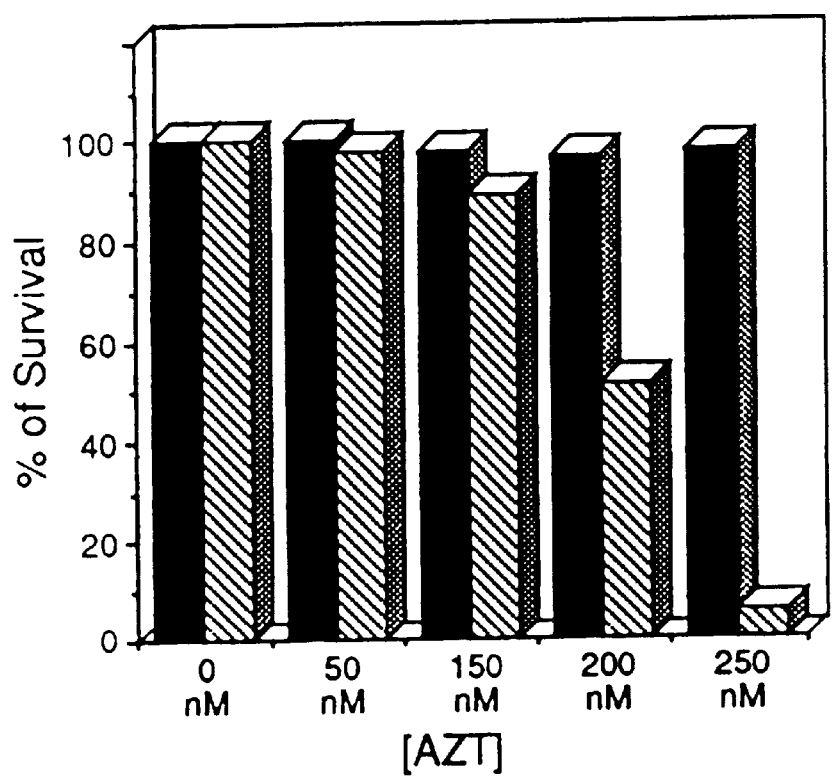
Figure 4C:
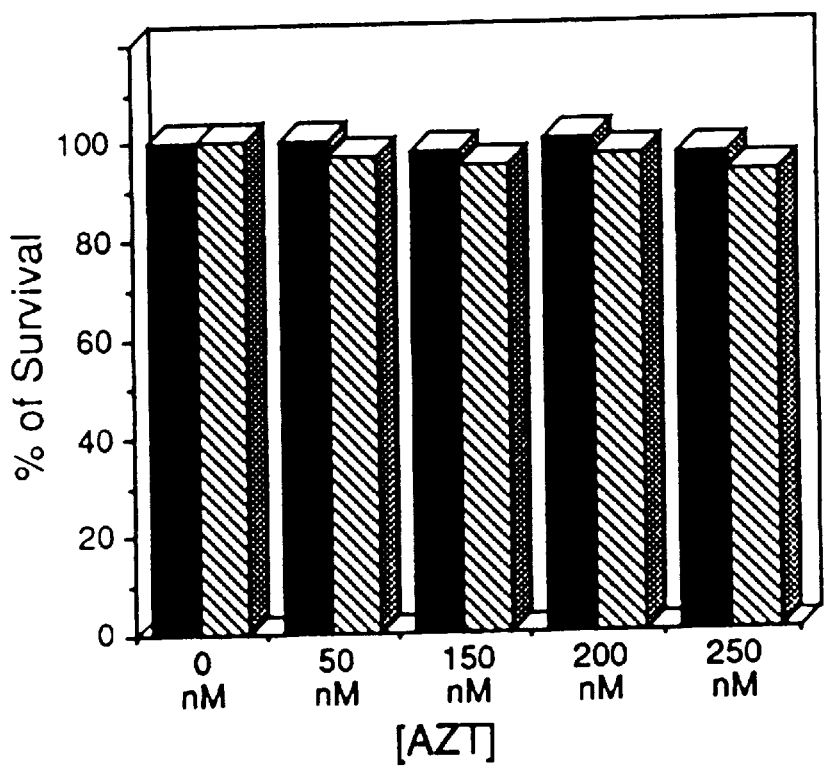

Another way to assay inhibitory effect of AZT on complementation system is to determine survival of colonies in the plates with or without AZT. Approximately 300 E. coli cells expressing the designated proteins (A: rat DNA polymerase β, B: wild-type HIV RT (pHIV RT-2), C: TY215 HIV RT) were plated in duplicate on nutrient agar containing tetracycline, chloramphenicol and IPTG (as described in FIG. 1) and AZT (0, 50, 150, 200 and 250 nM) and were incubated at 30° C. (black bar) or 37° C. (open bar) for 48 hr. The percent survival is the ratio of colonies formed in the presence and absence of AZT. As seen in FIG. 4A, Pol I$^{ts}$ expressing rat DNA polymerase β is able to grow even in high concentrations of AZT whereas the Pol I$^{ts}$ strain expressing HIV RT does not grow at high AZT concentrations (FIG. 4B). TY215, an HIV mutant obtained from a patient treated with AZT, contains a mutation in the RT gene that renders HIV RT resistant to AZT in vivo. As seen in FIG. 4C, cells expressing TY215 AZT resistant mutant are able to grow at high concentrations of AZT.

D. Alternative Selection Assays

The growth of the host cell is, alternatively, dependent on resistance to an antibiotic by the use of a plasmid that both contains an antibiotic resistance gene and requires DNA polymerase I for plasmid replication. This requirement can be substituted by HIV RT, thus rendering growth dependent on the expression of HIV RT.

1. Replication of pBR322 Plasmid Derivatives by HIV RT in Pol I$^{ts}$ Mutant.

a. Plasmids: An example of this is illustrated by the replication of pBR322 plasmid derivatives (e.g., pBS-SK from Stratagene, San Diego, Calif.), a plasmid that requires DNA polymerase I for replication initiation (Witkin and Roegner-Maniscalco, *J. Bacteriol.* 174:4166–4168, 1992; and Sweasy and Loeb, *Proc. Natl. Acad. Sci. USA* 90:4626–4630, 1993). This class of plasmids cannot be replicated in Pol I$^{ts}$ mutant at non-permissive temperature (37° C.–42° C.).

b. Introduction of the Plasmid into Host Cells: transformation of pBR322 to Pol I$^{ts}$ mutants containing pHIV RT and pHSG576 plasmids: 1 μg of pBR322 (obtained from Promega, Madison, Wis.) is transformed into the Pol I$^{ts}$ mutant cell containing pHSG576 or pHIV RT plasmids as described in section I.A.4., above. The transformed cells are plated to NA selection plates containing carbenicillin (50 mg/l), which is hereto forth designated as the pBR322 NA plate.

c. Test for HIV RT-dependent pBR322 Replication in Pol I$^{ts}$ Cells: Pol I$^{ts}$ cells containing pBR322 and either pHSG576 (lacking HIV RT) or pHIV RT plasmids are grown in NB media containing carbenicillin (50 mg/l) for 24 hours at 30° C. Grown cells are diluted and plated to pBR322 NA plates. Transformed cells were grown to 2×10$^8$ cells per ml in nutrient broth containing tetracycline (12.5 mg/l), chloramphenicol (34 mg/l), IPTG (1 mM) and carbenicillin (50 mg/l). Cells were diluted and plated to nutrient agar plates containing tetracycline, chloramphenicol, carbenicillin and IPTG as described above. Duplicate plates containing about 500 cells per plate are incubated at 30° C. and 37° C. for 48 hours. Plating efficiency of each strain at 37° C. is shown as the ratio of colonies grown at 37° C. to colonies at 30° C. (Table 1). In this example, the growth of the E. coli is dependent on the replication of the plasmid which confer the carbenicillin resistant phenotype.

TABLE 1

REPLICATION OF PBR322 ORIGIN BY HIV RT

| E. coli strain | polA + recA + wild-type | | polA12recA718 mutant | |
|---|---|---|---|---|
| plasmid | pHSG576 | pHSG576 | pHIV RT-2 | pHIV RT-3 |
| plating efficiency at 37° C. | 91% | 0.5% | 28% | 11% |

E. Alternative Complementation Systems

1. Other Vectors and Phages a. E. coli plasmids: This complementation assay is used with any E. coli plasmid that requires Pol I for replication (e.g., pGB2, 6).

b. A vector that contains any E. coli promoter is used for transcription of HIV RT gene.

c. E. coli phages (e.g., phage lambda) are used as expression vehicles for expression of HIV RT.

d. Bacteria other than E. coli (e.g., Salmonella, *Thermus quaticus* and *Bacillus subtilis*) are used in conjunction with host specific phage DNAs.

e. Other eucaryotic cells containing mutant DNA polymerases are adopted for these assays including mammalian cells with conditional mutants in one of the DNA polymerases. For example, mammalian cells such as a hamster cell line (Liu et al., *Proc. Natl. Acad. Sci. USA* 80:797, 1983), a human cell line (Dong et al., *J Biol. Chem.* 268:1, 1993), or a rat cell line (Chen et al., *Proc. Natl. Acad. Sci. USA* 91:3054–3057, 1994; Ezzeddine et al., *The New Biologist* 3:608–614, 1991) are used. Similarly, yeast may be used. The expression of HIV RT in yeast (e.g., *Saccharomyces cerevisiae*) is carried out with an appropriate yeast vector (e.g., pBK1). pBK1 is pYES2 (Invitrogen, San Diego, Calif.) containing the HIV RT gene (fused to the gal promoter). Expression of HIV RT in yeast is verified by western analysis. The ability of HIV RT to complement mutants with any of the known defects in DNA polymerase activity (vide infra) can be established.

f. Introduction of DNA expressing HIV RT to various host cells: For bacterial plasmids, a CaCl$_2$ procedure (Ausubel et al., *Short Protocols in Molecular Biology*, 2d ed., Greene Publishing Associates and John Wiley & Son, 1–24, 1993) or electroporation (Ausubel et al., *Short Protocols in Molecular Biology*, 2d ed., Greene Publishing Associates and John Wiley & Son, 1-25–1-27, 1993) is used. For phage DNA, in vitro packing system followed by transfection (Ausubel et al., *Short Protocols in Molecular Biology*, 2d ed., Greene Publishing Associates and John Wiley & Son, 1–39, 1993) is used. In the case of yeast, transformation, a lithium acetate procedure (Ausubel et al., *Short Protocols in Molecular Biology*, 2d ed., Greene Publishing Associates and John Wiley & Son, 13–29, 1993) or electroporation (Ausubel et al., *Short Protocols in Molecular Biology*, 2d ed., Greene Publishing Associates and John Wiley & Son, 13–28, 1993), is used.

2. Other Bacteria

The complementation system described in this application is applied to other bacteria known to have conditional mutants in DNA polymerase I or other DNA polymerase activities that are complemented by HIV RT.

a. *B. subtilis*: Mutants in DNA polymerase I are established by known genetic methods (Sambrook et al., *Molecular Cloning: A Laboratory Manual*, Cold Spring Harbor Laboratory, 1989). Of advantage is the fact that these cells are transfected at high efficiency and grown at a higher temperature than can *E. coli*.

b. Bacteria Strains that Grow at Elevated Temperatures: Many of these contain known mutants in DNA polymerase I.

3. Eucaryotic Cells a. Production of Eucaryotic Cells (e.g. *Saccharomyces cerevisiae*) with DNA polymerase conditional mutations (1) *Saccharomyces cerevisiae*: The CDC2 gene encodes yeast DNA polymerase III. Several temperature sensitive mutants of this allele (e.g., cdc2-1, cdc2-2) have been isolated (Conrad and Newlon, *Mol. Cel. Biol.* 3:1000–1012, 1983). cdc2 mutants have been shown to exhibit a growth defect at elevated temperatures and are also sensitive to alkylating agents (e.g., MMS) that cause DNA damage. Thus, yeast mutants are available for complementation by HIV RT.

b. Vector with HIV RT Gene: HIV RT gene is cloned into any one of a variety of yeast expression vectors (e.g., pYES2 from Invitrogen) that contain yeast specific promoters (e.g., gal P of pYES2). HIV RT is expressed in a form of fusion protein with yeast nuclear localization signal to facilitate delivery of HIV RT to the nucleus.

HIV RT gene was amplified with 5' Hind III RT primer and 3' Eco RI RT primer. 5' Hind III RT primer contains Hind III site and the sequence complementary with 5' end of HIV RT gene of pRT. 3' Eco RI primer contains Eco RI site and the sequence of 3' end of RT gene in pR. Amplified DNA was cloned to pYES2 vector at Hind III and Eco RI sites. Expression of HIV RT in yeast strain (CDC2$^+$) was observed by western analysis.

c. Introduction of Vectors to Eucaryotic Cells: Vectors expressing HIV RT or its fusion protein are transformed into yeast as described in section I.E.1.b., above.

d. Detection of Growth and Presentation of Inhibitor: The approach is analogous to that described above the *E. coli*. The medium and conditions are well known to those familiar with yeast genetics.

(1) Condition:

(a) cdc2-2: Cells harboring pYES2 or pBK1 (pYES2 with HIV RT gene) are grown in C-ura media (complete media) at 20° C.

(2) Detection of growth: Cells are exposed to MMS for different time intervals, and then plated and incubated in C-ura plates. Complementation by HIV RT is indicated by the finding that cdc2-2 harboring pBK1 are more resistant to MMS than cdc2-2 harboring pYES2. Other type of HIV RT constructs (e.g., fusion proteins, other vectors) are tested for complementation by a similar protocol.

e. HIV RT Inhibitors: Nucleoside analogs may have to be phosphorylated in yeast prior to inhibiting HIV RT or to be incorporated in yeast DNA and act as chain terminators. It may be desirable to co-express a nucleoside kinase that can phosphorylate the inhibitors that are to be evaluated. Either the genes can be directly introduced on the yeast chromosome or can be carried on the same plasmid as HIV RT.

F. Host Cells Additionally Containing Human Enzyme(s) to Phosphorylate Nucleosides or Nucleotides:

1. Gene Encoding Various Nucleoside Kinases

Genes expressing viral or human kinase (e.g., Herpes Simplex Virus Thymidine kinase:HSVTK) are introduced to Pol I$^{ts}$ cells expressing HIV RT by chromosomal integration (e.g., a phage lambda lysogen, bacterial transposons). *E. coli* contain an endogenous thymidine kinase that can phosphorylate thymidine and analogs of thymidine such as AZT (Munir et al., *Proc. Natl. Acad. Sci. USA* 90:4012–4016, 1993). Further phosphorylation by nucleotide kinases results in the production of nucleoside triphosphate analogs that are able to terminate DNA synthesis. Alternatively, it may be desirable to clone into *E. coli*, yeast, other bacteria, or eucaryotic cells, a gene that encodes the appropriate nucleoside kinases.

Figure 5A:
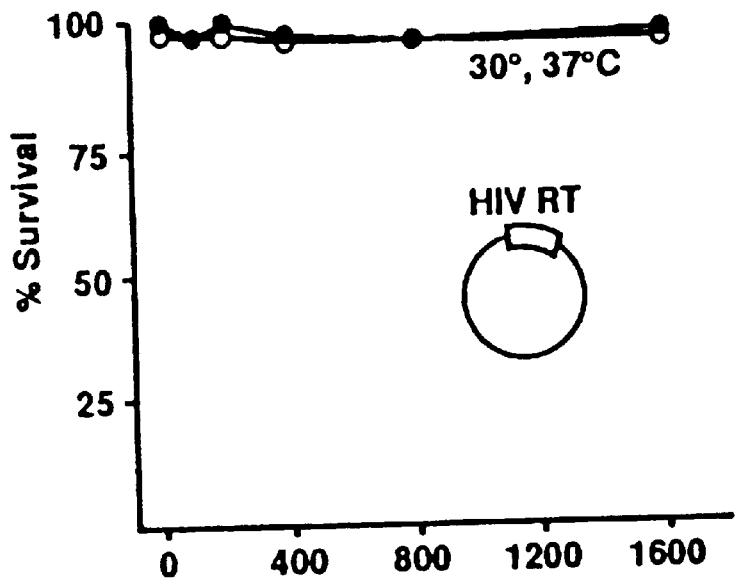
FIGS. 5A, 5B, 5C and 5D illustrates induction of ddC and AZT sensitivity of *E. coli* by co-expression of HSV TK and HIV RT. Approximately 250 Pol I$^{ts}$ cells harboring either pHIV RT-2 or pRT-TK were plated to NA plates containing different concentrations of ddC or AZT. Cells plated were incubated at 30° C. or 37° C. for 48 hrs. Survival of cells was determined by ratios of survived cells from NA plates with or without drugs.
Figure 5B:
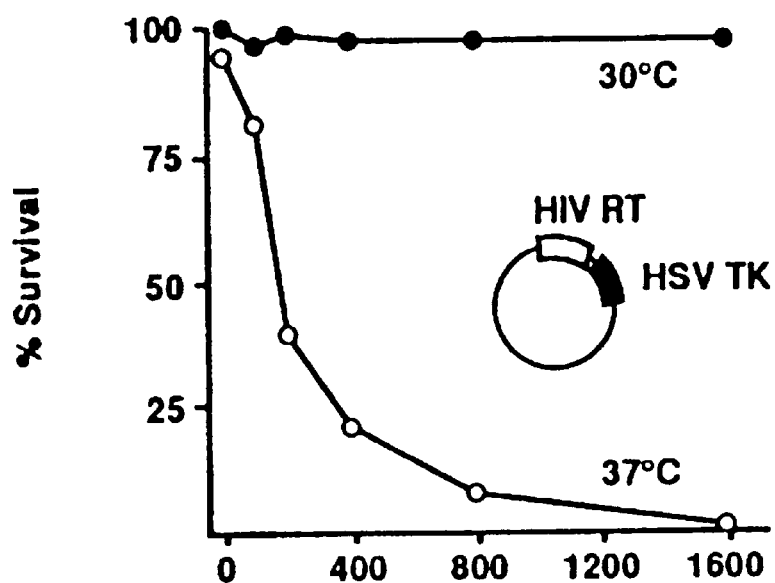
Figure 5C:
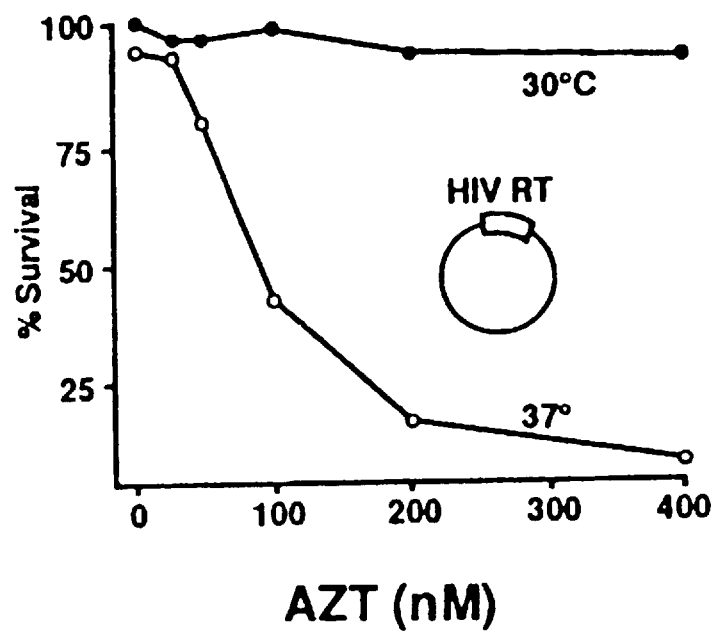
Figure 5D:
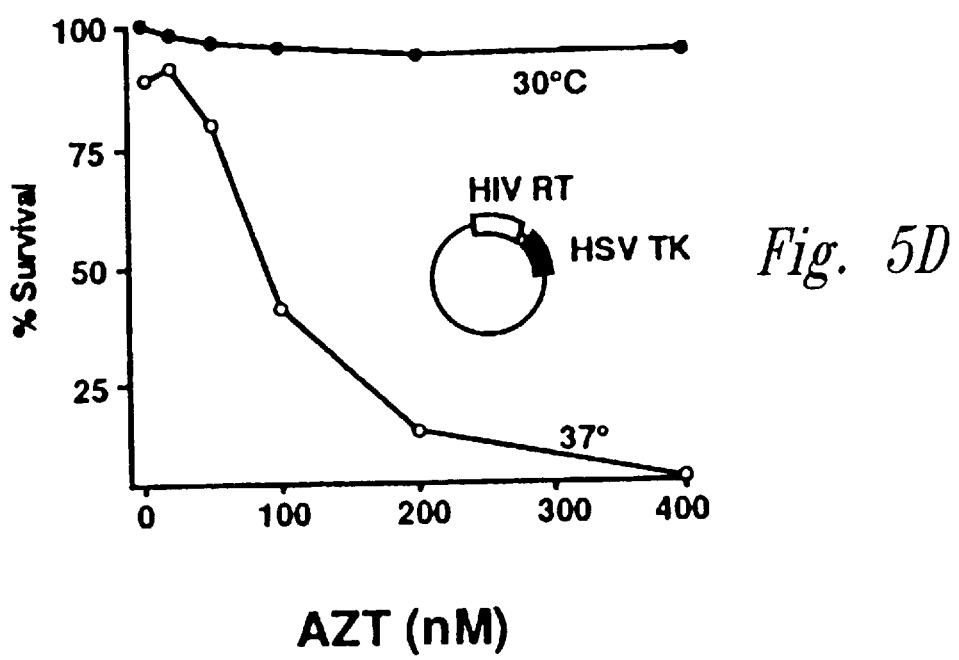

Herpes simplex thymidine kinase (HSV TK) was expressed as a vehicle to phosphorylate various types of nucleosides. HSV TK is able to phosphorylate dG, dC, dG as well as T analogs (Cheng, Y-C, *Biochem. Biophys. Acta* 452:370–381, 1976). A dual plasmid that contains the genes for both HIV RT and herpes thymidine kinase was constructed. The dual plasmid (pRT-TK) was assembled by introducing the wild type HSV TK gene into pHIVRT, the plasmid used in the basic complementation system. pHIVRT is a low copy number plasmid derived from pHSG576 that contains the gene for HIV RT under control of the lac P/O promoter. The inserted HSV TK gene contains a ribosome binding site for initiation of translation. HSV TK gene fused for ribosomal binding site was obtained from pET8c-HSVTK. The 1.1 kb XbaI/BamHI fragment of pET8c-HSVTK containing HSV TK gene was blunt-ended, and this fragment was inserted into blunt-ended EcoRl site of pHIVRT, generating pRT-TK. pTK is pHSG576 containing 1.1 Kb HSV TK at SmaI site. pHIVRT, pRT-TK and pTK contain DNA polymerase I-independent pSC101 replication origin from pHSG576 which is a low copy number plasmid. Both the HIV RT and HSV TK genes are under control of lac P/O and are transcribed within a single mRNA. In order to test the effect of ddC on growth of Pol I$^{ts}$ cells expressing HIV RT only or both HIV RT and HSV TK, about 300 cells were plated into NA plates. Survival of cells plated was determined as described in FIG. 3. The results indicate that the survival of *E. coli* harboring a plasmid that express solely HIV RT in place of Pol I is not effected by dideoxycytidine (FIG. 5A). In contrast, coexpression of herpes thymidine kinase and HIV RT render the *E. coli* sensitive to dideoxycytidine (FIG. 5B). In the control experiment, both the single and dual plasmids render the cells equally sensitive to AZT (FIGS. 5C and 5D). In other control experiments, it was confirmed that herpes thymidine phosphorylates dideoxycytidine and that herpes thymidine kinase and HIV RT are both expressed in these cells. The well-documented ability of herpes thymidine kinase to catalyze the phosphorylation of a variety of nucleoside analogs significantly expands the utility of this genetic complementation system.

2. Introducing Genes into the Cells: Phage DNAs and plasmid can be transformed into *E. coli* and yeast as described in section I.E.2.b., above.

G. Alternative Inhibitors:

For certain inhibitors, it may be desirable to vary conditions for solubility and for transport into host cells. Furthermore, the assay is used for the simultaneous testing of multiple compounds or for screening nucleoside libraries containing different substituents.

Example II

Screening Assay for HIV RT Mutants Exhibiting DNA Polymerase Activity

This assay is used to carry out structure function relationships with respect to the design of new inhibitors for HIV RT. Mutants of the enzyme can be established by site specific mutagenesis or by selection from random sequence libraries.

A. Production of HIV RT Genes Containing Mutations

1. Introduction of Specific Mutations in vitro: Site-directed mutagenesis (Ausubel et al., *Short Protocols in Molecular Biology*, 2d ed., Greene Publishing Association and John Wiley & Son, 8–3, 1993) is used to generate HIV RT mutant protein (e.g., TY215).

A plasmid containing a HIV RT gene encoding a HIV RT that is resistant to AZT (pHIV RT-4) was prepared based upon known HIV RT mutants (e.g., St. Clair et al., *Science* 256:1557–1559, 1991; Emini et al., *Nature* 364:679, 1993).

2. Introduction of HIV RT Containing Multiple Mutations: Oligomers containing multiple mutations are used for introducing multiple mutations and selecting HIV RT mutants that function as wild-type protein (e.g., genetic selection). Strategy for designing oligomers and detailed procedures have been previously described (Munir et al., *J. Biol. Chem.* 267:6584–6589, 1992). A segment of the HIV RT gene was replaced with an oligonucleotide that contains 10% random substitution at amino acid positions 67 to 78. This segment encodes a portion of the putative nucleotide binding site. The use of a partial random library increases the likelihood of substitutions involving one or a few amino acid residues and thus more closely mimics the spectrum of mutations obtained during the course of HIV infection. After transfection of *E. coli* polA12recA718, 600,000 transfectants were obtained, of which 2,000 grow at the non-permissive temperate and thus complemented DNA Pol 1. Each of two hundred positive clones sampled contains the plasmid that encodes HIV RT. The substituted segment within a sampling of the functionally active mutants was sequenced and each contains one or more nucleotide substitutions within the randomized position. Table 2 lists the amino acid substitutions from a sample of twenty active mutants (SEQ ID Nos. 3–22) obtained by random nucleotide substitutions, at positions 67–78.

TABLE 2

AMINO ACID SEQUENCES OF HIV RT MUTANTS

| | 67 | 68 | 69 | 70 | 71 | 72 | 73 | 74 | 75 | 76 | 77 | 78 |
|---|---|---|---|---|---|---|---|---|---|---|---|---|
| WT | Asp | Ser | Thr | Lys | Trp | Arg | Lys | Leu | Val | Asp | Phe | Arg |
| MT | | | | | | | | | | | | |
| 4 | ---- | ---- | ---- | ---- | ---- | ---- | ---- | ---- | ---- | Gly | ---- | ---- |
| 6 | ---- | ---- | ---- | Tyr | ---- | ---- | ---- | ---- | ---- | Val | ---- | Ser |
| 7 | Gly | His | ---- | ---- | ---- | ---- | ---- | ---- | ---- | Gly | ---- | ---- |
| 20 | ---- | ---- | Asn | ---- | ---- | ---- | ---- | ---- | ---- | ---- | ---- | ---- |
| 22 | ---- | ---- | ---- | Ile | ---- | ---- | ---- | ---- | Asp | ---- | ---- | Ser |
| 25 | ---- | ---- | ---- | ---- | ---- | ---- | Leu | ---- | ---- | ---- | ---- | ---- |
| 31 | ---- | ---- | ---- | Asn | ---- | ---- | ---- | Phe | ---- | ---- | Val | ---- |
| 45 | ---- | Thr | ---- | ---- | ---- | ---- | ---- | ---- | ---- | ---- | ---- | ---- |
| 50 | ---- | ---- | ---- | Ile | ---- | Ser | ---- | ---- | ---- | ---- | ---- | ---- |
| 52 | ---- | ---- | ---- | ---- | Cys | ---- | ---- | ---- | ---- | ---- | ---- | Gly |
| 58 | ---- | ---- | ---- | Asn | Cys | ---- | ---- | ---- | ---- | ---- | ---- | ---- |
| 59 | ---- | Ile | ---- | Asn | ---- | ---- | ---- | ---- | ---- | ---- | ---- | ---- |
| 60 | ---- | ---- | ---- | ---- | Leu | ---- | Asn | ---- | ---- | ---- | Thr | ---- |
| 61 | ---- | ---- | ---- | ---- | ---- | ---- | Arg | ---- | Asp | ---- | ---- | ---- |
| 62 | ---- | ---- | ---- | ---- | ---- | ---- | ---- | ---- | ---- | Val | ---- | ---- |
| 64 | ---- | ---- | ---- | ---- | ---- | ---- | ---- | ---- | ---- | Gly | ---- | ---- |
| 67 | Asn | ---- | ---- | ---- | ---- | Ser | Arg | ---- | ---- | ---- | ---- | ---- |
| 72 | ---- | ---- | ---- | ---- | ---- | ---- | ---- | ---- | ---- | ---- | Leu | ---- |
| 75 | ---- | ---- | Ala | ---- | Gly | ---- | ---- | ---- | ---- | ---- | ---- | ---- |

WT: wild-type sequence
MT: mutants selected
----: same as wild-type sequence

B. Vectors with Mutant HIV RT Introduction of Vectors into Host Cells and Growth of Host Cells The same protocols described in Example I are utilized.

Example III

Screening Assay to Tailor Therapeutic Regime to Individual Patient

The effectiveness of current nucleoside analogs used in the treatment of AIDS is limited by the rapid emergence of mutations in HIV RT, some of which reduce the affinity of the enzyme for the specific inhibitor (Larder et al., *Science* 243:1731, 1989). The new mutants are not only resistant to the analog used in the therapy, but frequently are also resistant to related analogs. The present complementation assay offers the evaluation of HIV RT from individual patients for susceptibility to inhibition by a panel of potential inhibitors, e.g., nucleoside analogs.

A. Preparation of Gene Encoding a HIV RT from Individual Patients

Samples of blood, tissue or other body fluids containing the AIDS virus are obtained from individual patients. Total genomic DNA with integrated viral DNA or viral RNA is isolated by conventional procedures (e.g., Sambrook et al., ibid.). Thereafter, a portion of or the entire gene for HIV RT is amplified using the polymerase chain reaction (e.g., Vartanian et al., *J. Virol.* 65:1779–20 1788, 1991). The primers contain overhanging sites to facilitate cloning in vectors described above.

B. Vector with Patient's HIV RT Gene

The vector used for the expression of the patient's HIV RT gene is the same as those used for expression of the wild type HIV RT.

C. Introducing Vectors Containing the Gene or a Portion of the Gene for HIV RT Into *E. coli* Mutants The procedure for introducing the vector and growth of the host cells is that described in Example I.

D. Testing Compounds for Inhibition of a Patient's HIV RT

The complementation assays described are used for testing a panel of known and approved nucleoside analogs and candidate inhibitors of HIV RT. Any putative mutations in HIV RT that evolve during the course of the disease that render the virus resistant to the current therapy being used to treat an individual patient may be susceptible to other HIV RT inhibitors or a combination of inhibitors.

From the foregoing, it will be evident that, although specific embodiments of the invention have been described herein for purposes of illustration, various modifications may be made without deviating from the spirit and scope of the invention.

What is claimed is:

1. A method of screening for compounds that inhibit reverse transcriptase of human immunodeficiency virus (HIV RT), comprising:
   (a) introducing a vector that expresses the gene encoding an HIV RT into a bacterial host cell or eucaryotic host cell in culture, said host cell containing a conditional mutant in the host cell gene encoding a DNA polymerase;
   (b) incubating said host cell harboring said vector under conditions that are limiting for the growth of the host cell in the absence of active HIV RT, said conditions further including a candidate compound which may be capable of inhibiting said HIV RT; and
   (c) detecting the presence or absence of growth, thereby determining whether said candidate compound inhibited said HIV RT.

2. The method of claim 1 wherein said vector is a plasmid that requires a DNA polymerase for replication and wherein said conditions are limiting for the growth of said host cell in the absence of replication of said plasmid.

3. The method of claim 2 wherein said conditions include an antibiotic to which said host cell is susceptible in the absence of replication of said plasmid.

4. The method of claim 1 wherein said host cell is a bacterial cell containing a conditional mutant in the gene encoding a DNA polymerase.

5. The method of claim 4 wherein said host cell is an *E. coli* polA12recA718 cell.

6. The method of claim 1 wherein said host cell is a yeast cell containing a conditional mutant in the gene encoding a DNA polymerase.

7. The method of claim 1 wherein said host cell is a mammalian cell containing a conditional mutant in the gene encoding a DNA polymerase.

8. The method of claim 1 wherein said vector is a plasmid, bacteriophage, virus, retrovirus or cosmid.

9. A method of screening for compounds that inhibit reverse transcriptase of human immunodeficiency virus (HIV RT), comprising:
   (a) introducing a vector that expresses the gene encoding an HIV RT into temperature sensitive *E. coli* polA12recA718 host cells, said host cells containing a conditional mutant in the host cell gene encoding a DNA polymerase such that growth of said host cells at a non-permissive temperature is dependent on expression of active HIV RT;
   (b) plating dilutions of said host cells harboring said vector onto a plate containing media sufficient for growth and containing a candidate compound which may be capable of inhibiting said HIV RT;
   (c) incubating said host cells harboring said vector at a temperature not permissive for growth of *E. coli* polA12recA718 cells that lack a DNA-dependent DNA polymerase activity at the non-permissive temperature; and
   (d) detecting the presence or absence of growth at low cell density, thereby determining whether said candidate compound inhibited said HIV RT.

10. The method of claim 1 or claim 9 wherein said host cells contain an additional gene encoding an enzyme able to phosphorylate nucleosides or nucleotides.

11. The method of claim 10 wherein said gene encodes a human or viral enzyme.

12. The method of claim 10 wherein said gene encodes a deoxynucleotide kinase.

13. The method of claim 1 or claim 9 wherein said vector expresses a gene for HIV RT that contains one or more mutations.

14. The method of claim 13 wherein step (b) includes two or more candidate compounds which may be capable of inhibiting a mutant HIV RT.

15. The method of claim 1 or claim 9 wherein said candidate compound is a nucleoside or nucleotide.

16. A method of screening for active human immunodeficiency virus reverse transcriptase (HIV RT) mutants, comprising:
   (a) introducing a vector that expresses the gene encoding an HIV RT mutant into a bacterial host cell or eucaryotic host cell in culture, said host cell containing a conditional mutant in the host cell gene encoding a DNA polymerase;
   (b) incubating said host cell harboring said vector under conditions that are limiting for the growth of the host cell in the absence of active HIV RT; and
   (c) detecting the presence or absence of growth, thereby determining whether said HIV RT mutant is active.

17. The method of claim 16 wherein said vector is a plasmid that requires a DNA polymerase for replication and wherein said conditions are limiting for the growth of said host cell in the absence of replication of said plasmid.

18. The method of claim 17 wherein said conditions include an antibiotic to which said host cell is susceptible in the absence of replication of said plasmid.

19. The method of claim 16 wherein said host cell is a bacterial cell containing a conditional mutant in the gene encoding a DNA polymerase.

20. The method of claim 19 wherein said host cell is an *E. coli* polA12recA718 cell.

21. The method of claim 16 wherein said host cell is a yeast cell containing a conditional mutant in the gene encoding a DNA polymerase.

22. The method of claim 16 wherein said host cell is a mammalian cell containing a conditional mutant in the gene encoding a DNA polymerase.

23. The method of claim 16 wherein said vector is a plasmid, bacteriophage, virus, retrovirus or cosmid.

24. A method of screening for active human immunodeficiency virus reverse transcriptase (HIV RT) mutants, comprising:
   (a) introducing a vector that expresses the gene encoding an HIV RT mutant into temperature sensitive *E. coli* polA12recA718 host cells, said host cells containing a conditional mutant in the host cell gene encoding a DNA polymerase such that growth of said host cells at a non-permissive temperature is dependent on expression of active HIV RT;
   (b) plating dilutions of said host cells harboring said vector onto a plate containing media sufficient for growth;
   (c) incubating said host cells harboring said vector at a temperature not permissive for growth of *E. coli* polA12recA718 cells that lack a DNA-dependent DNA polymerase activity at the non-permissive temperature; and
   (d) detecting the presence or absence of growth at low cell density, thereby determining whether said HIV RT mutant is active.

25. The method of claim 16 or claim 24 wherein said gene encoding the HIV RT mutant contains more than one mutation.

26. The method of claim 16 or claim 24 wherein said gene encoding the HIV RT mutant is obtained from a recombinant clone, a patient sample, synthetic assembly, or in vitro mutagenesis.

27. A method of screening for compounds that inhibit human immunodeficiency virus reverse transcriptase (HIV RT) obtained from a patient, comprising:
   (a) amplifying the gene for HIV RT from a sample from an individual infected with HIV;
   (b) introducing said HIV RT gene into a vector that expresses said HIV RT gene;
   (c) introducing said vector into a bacterial host cell or eucaryotic host cell in culture, said host cell containing a conditional mutant in the host cell gene encoding a DNA polymerase;
   (d) incubating said host cell harboring said vector under conditions that are limiting for the growth of the host cell in the absence of active HIV RT, said conditions further including a candidate compound which may be capable of inhibiting said HIV RT; and
   (e) detecting the presence or absence of growth, thereby determining whether said candidate compound inhibited said HIV RT from said individual.

28. The method of claim 27 wherein said vector is a plasmid that requires a DNA polymerase for replication and wherein said conditions are limiting for the growth of said host cell in the absence of replication of said plasmid.

29. The method of claim 28 wherein said conditions include an antibiotic to which said host cell is susceptible in the absence of replication of said plasmid.

30. The method of claim 27 wherein said host cell is a bacterial cell containing a conditional mutant in the gene encoding a DNA polymerase.

31. The method of claim 30 wherein said host cell is an *E. coli* polA12recA718 cell.

32. The method of claim 27 wherein said host cell is a yeast cell containing a conditional mutant in the gene encoding a DNA polymerase.

33. The method of claim 27 wherein said host cell is a mammalian cell containing a conditional mutant in the gene encoding a DNA polymerase.

34. The method of claim 27 wherein said vector is a plasmid, bacteriophage, virus, retrovirus or cosmid.

35. A method of screening for compounds that inhibit human immunodeficiency virus reverse transcriptase (HIV RT) obtained from a patient, comprising:
   (a) amplifying the gene for HIV RT from a sample from an individual infected with HIV;
   (b) introducing said HIV RT gene into a vector that expresses said HIV RT gene;
   (c) introducing said vector into temperature sensitive *E. coli* polA12recA718 host cells, said host cells containing a conditional mutant in the host cell gene encoding a DNA polymerase such that growth of said host cells at a non-permissive temperature is dependent on expression of active HIV RT;
   (d) plating dilutions of said host cells harboring said vector onto a plate containing media sufficient for growth and containing a candidate compound which may be capable of inhibiting said HIV RT;
   (e) incubating said host cells harboring said vector at a temperature not permissive for growth of *E. coli* polA12recA718 cells that lack a DNA-dependent DNA polymerase activity at the non-permissive temperature; and
   (f) detecting the presence or absence of growth at low cell density, thereby determining whether said candidate compound inhibited said HIV RT from said individual.

36. The method of claim 27 or claim 35 wherein said host cells contain an additional gene encoding an enzyme able to phosphorylate nucleosides or nucleotides.

37. The method of claim 27 or claim 35 wherein step (d) includes two or more candidate compounds which may be capable of inhibiting HIV RT.

38. The method of claim 27 or claim 35 wherein said amplifying in step (a) comprises amplifying by a polymerase chain reaction.

39. The method of claim 27 or claim 35 wherein said introducing in step (b) comprises cutting a vector with restriction enzymes and ligating said HIV RT gene.

40. An *E. coli* polA12recA718 cell line harboring a pHIV RT plasmid which substitutes for the deficient DNA polymerase of said *E. coli*.

41. A method for testing the biological effectiveness of candidate compounds for the inhibition of human immunodeficiency virus reverse transcriptase (HIV RT) in vivo, comprising:
   (a) introducing cells containing a vector that expresses the gene encoding an HIV RT into a test animal, said cells containing a conditional mutant in the cell gene encoding a DNA polymerase such that survival of said cells in said animal is dependent on expression of active HIV RT;
   (b) administering to said animal a compound in a pharmaceutically acceptable form, said compound a candidate for the inhibition of HIV RT; and
   (c) assessing the ability of said candidate compound to clear said cells from said animal, thereby determining whether said candidate compound inhibits HIV RT in vivo.

42. The e m method of claim 41 wherein said test animal is a mouse, rat, guinea pig, rabbit, cat, dog, swine or non-human primate.

43. The method o f claim 41 wherein said cells are bacterial cells.

44. The method of claim 43 wherein said bacterial cells are *E. coli* cells.

45. The method of claim 44 wherein said *E. coli* cells are polA12recA718 cells harboring a vector that expresses the gene encoding an HIV RT.

46. The method of claim 41 wherein said cells are pathogenic to said test animal.

47. The method of claim 46 wherein said cells are *Salmonella typhimurium*, said test animal is a mouse, and the step of assessing the ability of said candidate compound to clear said cells from said animal is based on survival of said animal.

48. The method of claim 41 wherein said candidate compound is a nucleoside or nucleotide.

49. A method for detecting in a blood sample from a warm-blooded animal the presence of an active compound that inhibits human immunodeficiency virus reverse transcriptase (HIV RT), comprising:
   (a) administering to a warm-blooded animal a compound that inhibits HIV RT, said compound in a pharmaceutically acceptable form;
   (b) isolating a blood sample from said animal; and
   (c) detecting the presence or absence of said compound by testing said blood sample in the method according to claim 1 wherein said blood sample replaces the candidate compound of said method, thereby determining whether said compound is present in active form in the blood of said animal.

50. The method of claim 49 wherein a blood sample is isolated from said animal at a plurality of times following administration of said compound.

* * * * *

UNITED STATES PATENT AND TRADEMARK OFFICE
CERTIFICATE OF CORRECTION

PATENT NO : 6,130,036
DATED : Oct. 10, 2000
INVENTOR(S) : Loeb et al.

It is certified that errors appear in the above-identified patent and that said Letters Patent are hereby corrected as shown below:

Claim 42, column 32, line 30, "The e m method of" should read --The method of--.
Claim 43, column 32, line 33, "The method o f" should read --The method of--.

Signed and Sealed this

First Day of May, 2001

*Attest:*

NICHOLAS P. GODICI

*Attesting Officer*    *Acting Director of the United States Patent and Trademark Office*

SEQUENCE LISTING

<160> NUMBER OF SEQ ID NOS: 22

<210> SEQ ID NO 1
<211> LENGTH: 43
<212> TYPE: DNA
<213> ORGANISM: Artificial Sequence
<220> FEATURE:
<223> OTHER INFORMATION: 5' RT primer used for amplification of HIV RT gene from pRT

<400> SEQUENCE: 1
gaagatctaa gcttaggagg ttgtcccata tgcccattag tcc				43

<210> SEQ ID NO 2
<211> LENGTH: 22
<212> TYPE: DNA
<213> ORGANISM: Artificial Sequence
<220> FEATURE:
<223> OTHER INFORMATION: 3' primer used for amplification of HIV RT gene
      from pRT

<400> SEQUENCE: 2
ttttgaattc gcatgcctgc ag				22

<210> SEQ ID NO 3
<211> LENGTH: 12
<212> TYPE: PRT
<213> ORGANISM: Human Immunodeficiency Virus

<400> SEQUENCE: 3

Asp Ser Thr Lys Trp Arg Lys Leu Val Asp Phe Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 4

Asp Ser Thr Lys Trp Arg Lys Leu Val Gly Phe Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 5

Asp Ser Thr Tyr Trp Arg Lys Leu Val Val Phe Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 6

Gly His Thr Lys Trp Arg Lys Leu Val Gly Phe Arg
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Randomly generated mutation of segment of HIV

```
        RT gene which encodes a portion of the putative
        nucleotide binding site

<400> SEQUENCE: 7

Asp Ser Asn Lys Trp Arg Lys Leu Val Asp Phe Arg
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Randomly generated mutation of segment of HIV
        RT gene which encodes a portion of the putative
        nucleotide binding site

<400> SEQUENCE: 8

Asp Ser Thr Ile Trp Arg Lys Leu Asp Asp Phe Ser
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Randomly generated mutation of segment of HIV
        RT gene which encodes a portion of the putative
        nucleotide binding site

<400> SEQUENCE: 9

Asp Ser Thr Lys Trp Arg Leu Leu Val Asp Phe Arg
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Randomly generated mutation of segment of HIV
        RT gene which encodes a portion of the putative
        nucleotide binding site

<400> SEQUENCE: 10

Asp Ser Thr Asn Trp Arg Lys Phe Val Asp Val Arg
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Randomly generated mutation of segment of HIV
        RT gene which encodes a portion of the putative
        nucleotide binding site

<400> SEQUENCE: 11

Asp Thr Thr Lys Trp Arg Lys Leu Val Asp Phe Arg
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Randomly generated mutation of segment of HIV
        RT gene which encodes a portion of the putative
        nucleotide binding site

<400> SEQUENCE: 12
```

```
Asp Ser Thr Lys Cys Arg Lys Leu Val Asp Phe Gly
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 13

Asp Ser Thr Ile Trp Ser Lys Leu Val Asp Phe Arg
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 14

Asp Ser Thr Asn Cys Arg Lys Leu Val Asp Phe Arg
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 15

Asp Ile Thr Asn Trp Arg Lys Leu Val Asp Phe Arg
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 16

Asp Ser Thr Lys Leu Arg Asn Leu Val Asp Thr Arg
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 17

Asp Ser Thr Lys Trp Arg Arg Leu Asp Asp Phe Arg
 1               5                  10
```

```
<210> SEQ ID NO 18
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 18

Asp Ser Thr Lys Trp Arg Lys Leu Val Val Phe Arg
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 19

Asp Ser Thr Lys Trp Arg Lys Leu Val Gly Phe Arg
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 20

Asn Ser Thr Lys Trp Ser Arg Leu Val Asp Phe Arg
 1               5                  10

<210> SEQ ID NO 21
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 21

Asp Ser Thr Lys Trp Arg Lys Leu Val Asp Leu Arg
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Randomly generated mutation of segment of HIV
      RT gene which encodes a portion of the putative
      nucleotide binding site

<400> SEQUENCE: 22

Asp Ser Ala Lys Gly Arg Lys Leu Val Asp Phe Arg
 1               5                  10
```